(12) United States Patent
Madasamy

(10) Patent No.: US 9,046,540 B2
(45) Date of Patent: Jun. 2, 2015

(54) ASSAY, COMPOSITION AND NON-ENZYMATIC MECHANISM OF STATIN IN MODULATING LIPID METABOLISM

(71) Applicant: Shanmugavel Madasamy, Cupertino, CA (US)

(72) Inventor: Shanmugavel Madasamy, Cupertino, CA (US)

(73) Assignee: Plaxgen Inc., Fremont, CA (US)

( * ) Notice: Subject to any disclaimer, the term of this patent is extended or adjusted under 35 U.S.C. 154(b) by 0 days.

(21) Appl. No.: 14/477,748

(22) Filed: Sep. 4, 2014

(65) Prior Publication Data

US 2015/0011426 A1    Jan. 8, 2015

Related U.S. Application Data

(63) Continuation-in-part of application No. 12/286,368, filed on Sep. 29, 2008, now Pat. No. 8,932,558, and a continuation-in-part of application No. 13/684,027, filed on Nov. 21, 2012.

(51) Int. Cl.
    *G01N 33/92*      (2006.01)
    *A61K 49/00*      (2006.01)
    *G01N 33/94*      (2006.01)

(52) U.S. Cl.
CPC ............ *G01N 33/92* (2013.01); *G01N 2500/02* (2013.01); *A61K 49/0008* (2013.01); *G01N 33/94* (2013.01)

(58) Field of Classification Search
CPC .......... A61K 49/0008; G01N 2500/00; G01N 2500/02; G01N 2500/20; G01N 2570/00; G01N 33/68; G01N 33/6896; G01N 33/92
USPC ................. 436/63, 71, 164, 172, 173; 435/11
See application file for complete search history.

(56) References Cited

FOREIGN PATENT DOCUMENTS

WO      2013/081946     *   6/2013

* cited by examiner

*Primary Examiner* — Maureen Wallenhorst
(74) *Attorney, Agent, or Firm* — Geeta Kadambi; Riddhi IP LLC

(57) ABSTRACT

A novel non-enzymatic assay for lipid modulating drugs is being described for biological samples. For the first time non-enzymatic mechanism of statin drugs in modulating lipid aggregates and forming lipid particles is being shown. A simple flow cytometer based testing for detection of lipid particles, the effect of lipid modulating drug such as statin in vitro and testing for efficacy of the drug for an individual, dosage adjustment and drug discovery mechanism is being described. The lipid modulating drugs either individually or in combination can be discovered, optimized or efficacy tested using this assay. A novel statin induced lipid particle formation described can be used for diagnosis, personalized medicine and biomarker identification as well.

19 Claims, 17 Drawing Sheets

ASSAY, COMPOSITION AND NON-ENZYMATIC MECHANISM OF STATIN IN MODULATING LIPID METABOLISM

CROSS-REFERENCE TO RELATED APPLICATIONS

This application claims priority to and is a continuation-in-part (CIP) of both U.S. application Ser. No. 12/286,368 filed on Sep. 29, 2008 and U.S. application Ser. No. 13/684,027, filed on Nov. 21, 2012.

FIELD OF INVENTION

This application discloses discovery of a novel non-enzymatic statin mechanism, method and composition for modulating lipid particles formation, development of statin response assay and biomarkers as composition to identify statin-lipid/cholesterol particles.

BACKGROUND

Atherosclerosis is a chronic inflammatory cardiovascular disease (CVD) caused mainly due to dyslipidaemia, lipoprotein oxidation, disturbance of blood flow and endothelial dysfunction. Dyslipidemia is characterized by high levels of triglycerides, low levels of high density lipoproteins (HDL) and elevated levels of low-density lipoprotein cholesterol (LDL) concentrations in affected patients (Chapman M J, 2011). Atherosclerosis related CVD still remains the leading cause of worldwide morbidity and mortality. Clinical and epidemiological studies have demonstrated elevated level of LDL particles is an early event in initiation and progression of atherosclerosis. In addition, reduced HDL is known to be associated with increased risk of developing CVD. (Kishida K et al 2.012) The HDL particles are heterogeneous in shape, density, size, composition and they play a key role in athero-protective functions such as reverse cholesterol transport (RCT), anti-oxidant, anti-inflammatory, and antithrombosis (Kishida K et al 2013). The RCT mediated promotion of cholesterol efflux from foam cell macrophages of atherosclerotic lesions and its return to the liver for ultimate biliary excretions are important process by which HDL particles protect against atherosclerosis. It is scientifically well established that LDL and very low density lipoproteins (VLDL) promote atherosclerosis leading to the damage of blood vessels whereas HDL, act as an athero-protective system, to mitigate the damages on the blood vessel wall (McTaggart F, Jones P, 2008). Accordingly, reducing LDL particles and promoting HDL particles concentration by drugs is proven to reduce the risk of developing atherosclerosis related CVD.

Statin has become a leading cardiovascular medicine prescribed to treat patients for preventing both primary and secondary incidences of CVD (Davidson M H, 2005). Different types of statin drugs, brand names and their chemical structures are shown in the Table 1. Based on soluble property, statins are broadly divided into two categories such as hydrophilic and lipophilic. For example, statins such as pravastatin and rosuvastatin possess polar side groups bound to hydrophobic ring, rendering them hydrophilic, while pitavastatin, atorvastatin, lovastatin and simvastatin are classified as lipophilic. The difference in chemical structures of the statins plays a significant role in the metabolism of these drugs. For example, lovastatin and simvastatin, circulate in the blood as an inactive prodrug, whereas atorvastatin and rosuvastatin circulate as biologically active drugs. Active statins competitively inhibit HMG-CoA reductase, the rate-limiting enzyme in the mevalonate pathway involved in cell mediated cholesterol synthesis (Endo A, 1992).

In addition, statins play important role in the clearance of circulating atherogenic LDL particles by up-regulating LDL receptors and thus contributing to about 24% reduction in CVD deaths as demonstrated in a number of clinical trials (Xanthopoulou I et al 2013). Although intensive use of statins leads to reduction in LDL levels the overall atherosclerosis related CVD mortality still remains high. It is being increasingly recognized that circulating levels of HDL are inversely correlated with CVD mortality suggesting HDL is an attractive target for statin and combination therapy to further reduce the residual risk from cardiovascular events (Chapman Mi et al, 2010).

Given the fact that statins are pleiotropic molecules and are being extensively used to treat CVD it is important to further understand their mechanism of action particularly related to lipid metabolism (Davignon J, 2012). Currently, there is no assay available to determine the effect of each statin on lipid particles formation in biological samples. Hence, there is a major need for the development of robust, reliable, and mechanism based assays.

SUMMARY

In the instant invention a discovery of a novel non-enzymatic mechanism to observe the modulation of lipid aggregates by the lipid modulating drug to induce lipid particle formation, in one embodiment. In another embodiment, detection of these lipid particles as different fractions is disclosed using various detection mechanisms. In one embodiment, the present application also discloses a novel non-enzymatic mechanism of a statin in regulating LDL and HDL particles formation in biofluids, development of a statin response test and proteomics based biomarkers identification in lipid/cholesterol particles in vitro.

In one embodiment, a non-enzymatic method for detecting modulation of lipid particles after the addition of lipid modulating drugs in biofluids having lipid aggregates is observed. In another embodiment, adding a lipid modulating drug at a specific concentration to a solution of a lipid aggregate having a second specific concentration. Once the addition has happened the mixture is incubated for a specific time. As another embodiment, detection is performed for the resultant combination effect on the lipid particle using an identification process. The identification process may be using a Flow cytometer, Nuclear Magnetic Resonance, ultra-centrifugation, gradient gel electrophoresis, ion mobility, fluorescence particle detectors and colorimetric method.

In one embodiment, lipid modulating drug is at least one of an ovastatin, simvastatin, atorvastatin, pravastatin, fluvastatin, rosuvastatin, pitavastatin and a combination thereof. In another embodiment, the resultant combination is a result for an efficacy of at least one of the ovastatin, simvastatin, atorvastatin, pravastatin, fluvastatin, rosuvastatin, pitavastatin and the combination thereof. In another embodiment, the combination thereof is at least one of the ovastatin, simvastatin, atorvastatin, pravastatin, fluvastatin, rosuvastatin, pitavastatin and another drug such as fibrates and niacin. In one embodiment, the lipid aggregate is at least one of a total lipid, derivative of total lipid, total cholesterol, derivative of a cholesterol, total triglycerides, a derivative of a triglyceride and a combination thereof.

In one embodiment, the solution of the lipid particle has at least one of total cholesterol, total triglycerides, LDL, HDL, non-HDL lipid, combination thereof solution and a serum. In one embodiment, the resultant combination effect is modulating effect and in turn it may lower one fraction of the lipid aggregate and increasing another fraction of the lipid aggregate.

In one embodiment, the non-enzymatic mechanism of statins and the lipid modulating drugs disclosed herein has applications in efficacy determination of the lipid modulating drug in vivo, medical diagnosis, personalized medicine, drug discovery and drug development, statin response test for CVD diagnosis, personalized statin therapy and anti-atherosclerosis therapy, statin response test for biomarker discovery and proteomics analysis, efficacy of drug in pre-clinical animal models and biofluids and use of statin-lipid complexes and their particles compositions for diagnosis and as therapeutics.

In one embodiment instructions teaching the use of the statin response assay kit according to the various methods and approaches described herein are provided. Such kits may also include information, such as scientific literature references, package insert materials, clinical trial results, and/or summaries of these and the like, which indicate or establish the activities and/or advantages of the agent. Kits described herein can be provided, marketed and/or promoted to health providers, including physicians, nurses, pharmacists, formulary officials, and the like.

In one embodiment, a biological sample is a biological fluid wherein the biological fluid is selected from the group consisting of blood, plasma, serum, cerebral spinal fluid, urine and saliva. In another embodiment, a biological fluid may be a clinical or a non-clinical fluid sample.

In another embodiment, the present disclosure also relate to a kit comprising: collecting a biological sample from a subject, contacting it statin and lipid aggregates; estimating HDL and LDL lipid particle; segregating and isolating the cholesterol particle and analyzing the biomarker. In most embodiments, the present disclosure relates to a kit for estimating a biomarker for CVD in a biological sample from a subject which may be a person or a patient at risk of having, suspected of having atherosclerosis.

The non enzymatic assay, composition and lipid modulating drug and lipid particle composition has been disclosed as an in vitro and in vivo method for drug discovery, drug efficacy testing and a novel non enzymatic behavior of statins in modulating lipid metabolism. Other features will be apparent from the accompanying drawings and from the detailed description that follows.

In one embodiment, the present disclosure further relates to a method of screening a candidate agent as a lipid modulating agent. The candidate agent may act to inhibit or accelerate the non-enzymatic mechanism of statins. The method of screening a candidate agent as disclosed, comprises: adding statin and a lipid aggregate in a solution or biological sample from a subject; adding the candidate agent or libraries of candidate agents; analyzing resulting samples for detection of lipid particle profile; The candidate agent may be added before the contacting or after the contacting with the biological sample. In most embodiments, the biological sample where the candidate agent is not added before and after the contacting is considered as a control sample for screening methods. A candidate agent, may include but not limited to a chemical compound, a small molecule, a therapeutic drug, a biological molecule, a natural compound, a natural or a synthetic oligomer, a ligand, a protein, an antibody and/or other component capable of rearranging the lipid particles profile or fractions in the presence or absence of biological sample. The screening method will further identify candidate agent for their potential as therapeutics for treating dyslipidemia related CVD.

The non-enzymatic assay, composition and lipid modulating drug and lipid particle has been disclosed as an in vitro and in vivo method for drug discovery, drug efficacy testing and a novel non-enzymatic behavior of statins in modulating lipid metabolism. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which.

Figure 1:
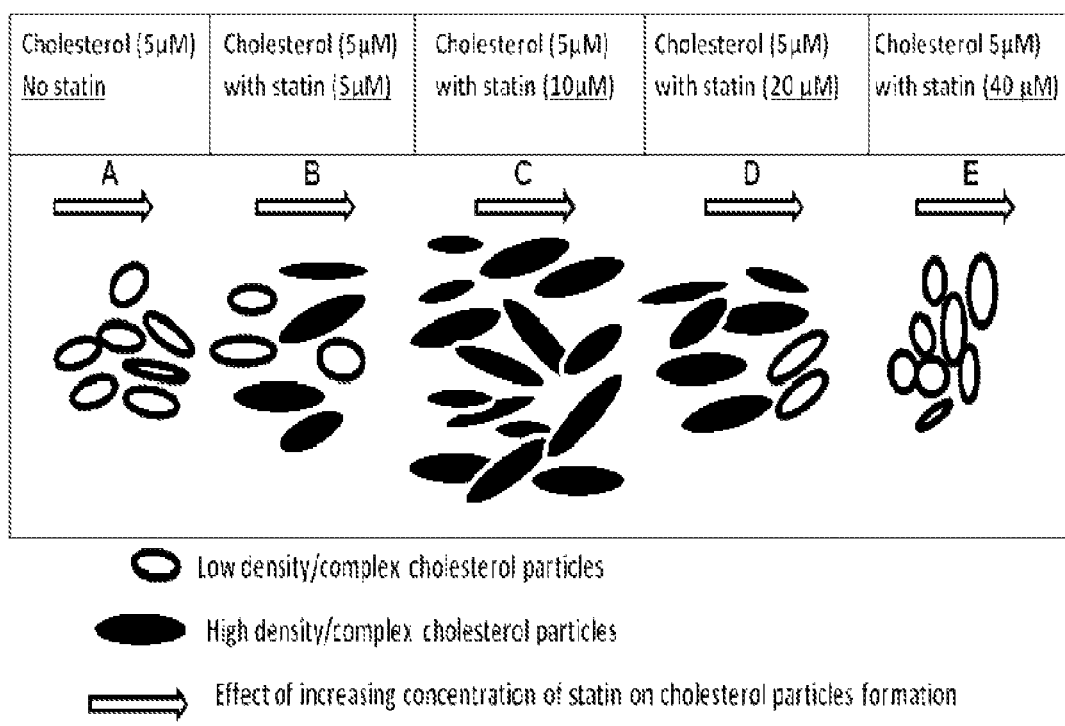
FIG. 1 represents a schematic of the non-enzymatic mechanism of statins mediated lipid particles formation.

Other features of the present embodiments will be apparent from the accompanying drawings and from the detailed description that follows.

DETAILED DESCRIPTION

Several method for a novel non-enzymatic assay for drug discovery, efficacy testing and dosage optimization, resultant analysis of the fraction of lipid particle and specifically novel non-enzymatic mechanism of statin drug for modulating lipid in biofluids are described. Although the present embodiments have been described with reference to specific example embodiments, it will be evident that various modifications and changes may be made to these embodiments without departing from the broader spirit and scope of the various embodiments.

In this instant disclosure a novel assay and a non-enzymatic reaction to predict the effect of statins in regulating LDL and HDL particles formation in the serum and plasma samples is being described. Earlier, Madasamy S (2012) has described development of a plaque array method for detection, quantitation and characterization of serum derived lipid and amyloid plaque particles. The plaque array method employs combination of Flow cytometer and Mass spectroscopy based proteomics approach for detection and biomarker identification in serum derived plaque particles. There is need for a tool to perform more tests for lipid particle modulating tests that are effective for personalized medicine and reducing side effects of over dosage is being discussed in the following paragraphs.

Materials and Methods

General method of conducting this novel non-enzymatic method would comprise of adding a lipid modulating drug at a specific concentration to a solution of a lipid having a second specific concentration to form a lipid-lipid modulating drug solution; incubating the lipid-lipid modulating drug solution for a specific time; detecting a resultant combination effect as a lipid particle using an identification process. A solution of the lipid may be defined as lipid or lipid aggregates that are generally present in the biofluids such as serum or plasma. In addition, a solution of lipid as stated in other parts of the application may be an individual solution of commercially available lipids and lipid aggregates or it may be a combination of both. Lipid-lipid modulating drug solution is a composition consisting of the lipid lowering drug that was chosen for the non-enzymatic assay and the above mentioned lipid. The lipid particle is defined as the result of the reaction that takes place between the lipid modulating drug and the lipid as is separated as a fraction. Lipid as it exists may be composed of more than one fraction.

Preparation of cholesterol and phospholipids aggregates: Cholesterol and phospholipid aggregates (lipid solution) were prepared as described earlier (Madasamy S, 2009; 2012). Briefly, fluorescence-labeled lyophilized cholesterol (1 mg) (Ex/Em=495 nm/507 nm) powder was solubilized in 1 ml of 100% alcohol. After centrifugation for 5 min at 5,000 rpm the supernatants were used as stock solution. From this stock solution, 100 µl was taken and mixed in 900 µl of phosphate buffer saline (PBS) solution for preparation of fluorescent-labeled cholesterol aggregates. Similarly, fluorescence-labeled lyophilized phospholipid (1 mg) (Ex/Em=495 nm/507 nm) powder was solubilized in 1 ml of 100% alcohol. After centrifugation for 5 min at 5,000 rpm the supernatants were used as stock solution. From this stock solution, 100 µl was taken and mixed in 900 µl of PBS for preparation of fluorescent-labeled phospholipid aggregates. The aggregates (5 µg) were analyzed by flow cytometry for detecting presence insoluble particles. The supernatant containing aggregates with no fluorescence positive particles or containing less than 300 particles/mL were used for binding with statins in the presence or absence of serum/plasma samples.

Preparation of statins for probing their effect on lipid particles formation: Lyophilized powders of Simvastatin, Ovastatin, Loavastatin, Atorvastatin, Pravastatin and Rosuvastatin were individually solubilized in 1 ml of 100% alcohol or other organic solvents to make 2.5 mM stock solution. After centrifugation for 5 min at 5,000 rpm the supernatants were used as stock solution. From this stock solution, increasing doses (5, 10, 20 and 40 µM) were prepared and mixed in 200 µl of PBS for incubation with phospholipid or cholesterol aggregates to examine statin induced effect on lipid particles formation. Similarly, lyophilized powders of Fluvastatin were solubilized in 1 ml of deionizer water to make 2.5 mM stock solution. After centrifugation for 5 min at 5,000 rpm the supernatants were used as stock solution.

Flow cytometer based detection of statin induced effect on lipid particles formation: From each stock solution of statins, increasing doses (5, 10, 20 and 40 µM) were prepared in 200 µl of PBS followed by the addition of phospholipid or cholesterol aggregates. After incubation at 37° C. for 1 hr the resulting samples were acquired by flow cytometer for detection and quantitation of Low complex cholesterol/lipid (LC-Chl) and High complex cholesterol/lipid (HC-Chl) particles formation. The samples were acquired by using settings with excitation 488 nm and emission detection at 520 and 560 nm. From each sample 2000 particles were acquired separately and total particles counts were measured. The concentration of particles in the samples was calculated by the software based on counting of number of particles/volume.

Flow cytometer based detection of statin mediated lipid particles formation in serum samples: In order to develop a statin response assay for determining their effect on LC-Chl and HC-Chl formation the following steps were followed. For detection of statin induced cholesterol plaque particles formation in the serum samples, each assay was performed in a 200 µl reaction (1900 of diluted serum 20%, 10%, 5% and 2%) to which statins (5 µM and 10 µM) were individually added followed by addition of fluorescence labeled cholesterol aggregates (5 µM). After incubation at 37° C. for 1 hr, the samples were acquired by flow cytometer for detection and quantitation of LC-Chl and HC-Chl particles formation.

Flow cytometer based sorting and isolation of lipid particles: To evaluate the composition of LC-Chl and HC-Chl particles to identify serum components, serum samples treated with statin were used for sorting and isolation of the resulting lipid particles. Each assay was performed separately in 1 mL reactions containing 800 µL of 30% serum in PBS spiked with individual statin (10 µM) followed by addition of cholesterol aggregates (10 µM). The mixtures were incubated at 37° C. for 1 h and insoluble particles formed in the presence of statin were sorted using a FACS Aria II Flow cytometer (BD Biosciences, San Jose, Calif., USA). Two fractions of cholesterol particles were gated on the fluorescence plot to permit separate sorting and isolation of high complex and low complex cholesterol particles (separate fractions). In other words adding a statin drug at a specific concentration and a lipid aggregate to form a lipid particle; capturing a lipid particle profile formed by the addition of the statin drug to the lipid aggregate; and modulating the specific concentration of the statin drug to a duplicate lipid aggregate to predict an effect of the statin drug may be performed.

Processing of isolated particles for mass spectroscopy-based proteomics analysis: Isolated lipid particles were centrifuged at 10000 rpm for 5 min and the pellet containing particles were resuspended in 100 µl PBS buffer. For trypsin digestion, 100 µl of LC-C and HC-C particles (2000 particles containing ~70 µg proteins) were precipitated with cold acetone (−80° C.) by adding 4x's the volume. Samples were placed on dry ice for 10 min with intermittent vortexing. Next, the samples were centrifuged at 4° C. at 10000 G for 10 min and the top layer of acetone was removed carefully. The samples were dried by speed vac for 10 min. The lipid particle pellets were reconstituted with 150 8M Urea, 100 mM ammonium bicarbonate followed by addition of 20 µl protease max solution. The samples were subjected to low level sonication followed by addition of 1.6 µl (500 mM) DTT. Tubes were incubated at 55° C. for 30 minutes and then brought to room temperature (RT). To each sample, 3.2 µl of 1M acrylamide was added and incubated at RT for 30 minutes. Next, 63 uL of 50 mM ammonium bicarbonate was added for a final volume of 98 µl followed by 20 of trypsin (2 µg, Trypsin/Lys C Mix) and the samples were incubated overnight at 37° C. The cryptic digests were quenched and acidified by adding 10 µl of 10% formic acid/water. The samples were purified using stage tip and used for MS/MS analysis.

Mass Spectroscopy analysis of samples and database search for identification of proteins: All trypsin digested samples were analyzed using Sequest (Thermo Fisher Scientific, San Jose, Calif., USA; version 1.0). Sequest was set up to search the Stanford uniprot Human database. Sequest was searched with a fragment ion mass tolerance of 1.00 Da and a parent ion tolerance of 20 PPM. Propionamide of cysteine was specified in Sequest as a fixed modification. Oxidation of methionine and phospho of serine, threonine and tyrosine were specified in Sequest as variable modifications. Scaffold (version Scaffold_4.2.1, Proteome Software Inc., Portland, Oreg., USA) was used to validate MS/MS based peptide and protein identifications. Peptide identifications were accepted if they could be established at greater than 95.0% probability by the Peptide Prophet algorithm with Scaffold delta-mass correction. Protein identifications were accepted if they could be established at greater than 99.0% probability and contained at least 2 identified peptides. Protein probabilities were assigned by the Protein Prophet algorithm. Proteins that contained similar peptides and could not be differentiated based on MS/MS analysis alone were grouped to satisfy the principles of parsimony. Protein identifications were accepted if they could be established at greater than 99.0% probability and contained at least 1 identified peptide. Proteins sharing significant peptide evidence were grouped into clusters.

Results

Numerous clinical trials have demonstrated the clinical advantages of using lipid-modulating statin therapy to reduce low density cholesterol (LDL-C) levels and incidence of cardiovascular events. Although statin therapy is effective they did not eliminate the cardiovascular risk entirely and a significant residual cardiovascular risk still remains. It is being increasingly recognized that the residual cardiovascular risk may stems from low levels of high density cholesterol (HDL-C) and elevated triglycerides in the blood. Accordingly, raising HDL-C induced by statins and other drugs is an attractive approach for reducing the residual risk of cardiovascular events (Cziraky M J et al, 2008). Drugs such as niacin and fibrates either alone or in combination with statins are being used for raising HDL-C levels (Wright R S, 2013). Importantly, from scientific and assay development point of view, the mechanism by which statins mediated increase in HDL-C is not known. In the present application we have developed a simple, cost effective biochemical assays that helps to better understand the statin novel mechanism for altering the profile of lipid particles formation. FIG. 1 includes both a schematic diagram and steps involved in the demonstration of non-enzymatic mechanism of statins in modulating lipid particles formation. The statin mediated effect on regulating profiles of lipid particles formation can be detected using multiple systems. The examples of such methods or systems are flow cytometer, Nuclear Magnetic Resonance, fluorescence particles detector, Mass spectroscopy, ion mobility, particles fraction separator and other colorimetric methods.

FIG. 1 represents a schematic of the non-enzymatic mechanism of statins mediated lipid particles formation. Step A, lipid particles formation in the absence of statin. Step B, effect of statins (5 µM) on Low complex and High complex lipid particles formation, Step C, increase in statin (10 µM) dose induced formation of mostly high complex lipid particles formation, Step D and E show further increase in the dose of statins (20-40 µM) cause low and very low complex lipid particles formation.

Figure 2A:
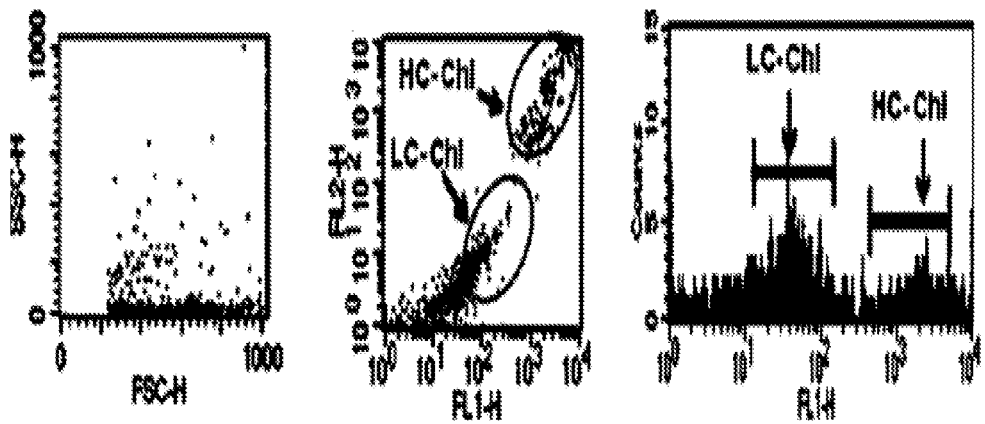
FIG. 2 (A and B) shows a Flow cytometer based detection of cholesterol and phospholipid plaque particles.
Figure 2B:
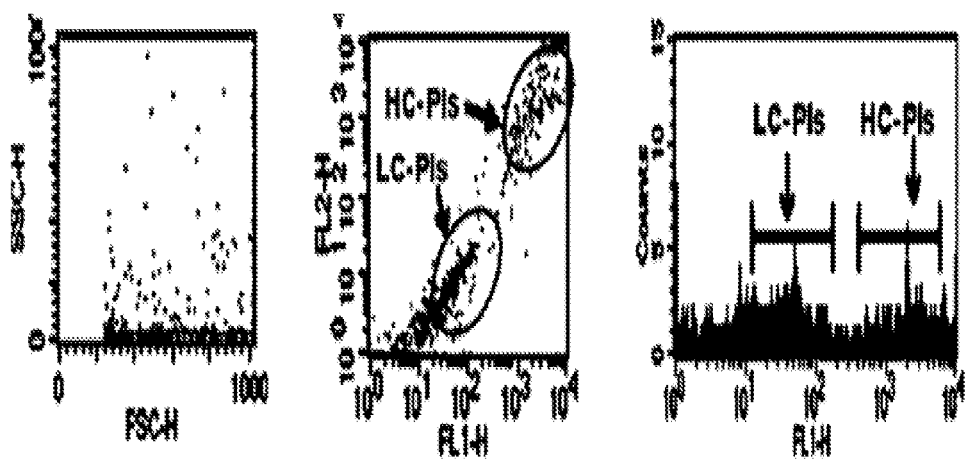

Flow cytometer based detection of self formation of Low complex and High complex cholesterol particles: As a first step to probe the mechanism of statin on lipid particles formation, we analyzed self-formation of cholesterol particles using flow cytometer. The fluorescence cholesterol aggregates incubated in the PBS cause self-formation of two major fractions; low complex (LC-Chl) and high complex (HC-Chl) cholesterol particles. This result suggests that cholesterol aggregates when incubated in the PBS buffer have property to slowly self assemble into LC-Chl and HC=Chl particles (FIG. 2A). The self assembly of cholesterol aggregates into insoluble LC-Chl and HC-Chl is a concentration and time dependent process. Similarly, phospholipid aggregates incubated in PBS led to self formation of low complex (LC-Pls) and high complex (HC-Pls) phospholipid particles (FIG. 2B). Together, these results confirm our earlier finding of property of lipid aggregates to self assemble into insoluble low complex and high complex lipid particles (Madasamy, 2012).

FIG. 2, Flow cytometer based detection of cholesterol and phospholipid plaque particles. Row A—left, acquisition dot plot analysis of cholesterol plaque particles, X axis represents forward scattering and Y axis represents side scattering; Row A—Middle, fluorescence positive cholesterol particles, X axis represents plaque particles detection in green channel (520 nm) and Y axis represents plaque particles detection in yellow channel (560 nm); Row A—Right, histogram plot showing two major fractions of cholesterol. Low complex cholesterol (LC-Chl) and High complex cholesterol (HC-Chl) particles. Row B—left, acquisition dot plot analysis of phospholipid plaque particles, X axis represents forward scattering and Y axis represents side scattering; Row B—Middle, fluorescence positive phospholipid particles, X axis represents plaque particles detection in green channel (520 nm) and Y axis represents plaque particles detection in yellow channel (560 nm); Row B—Right, histogram plot showing two major fractions of phospholipid particles. Low complex cholesterol (LC-Pls) and High complex cholesterol (HC-Pls) particles.

Figure 3A:
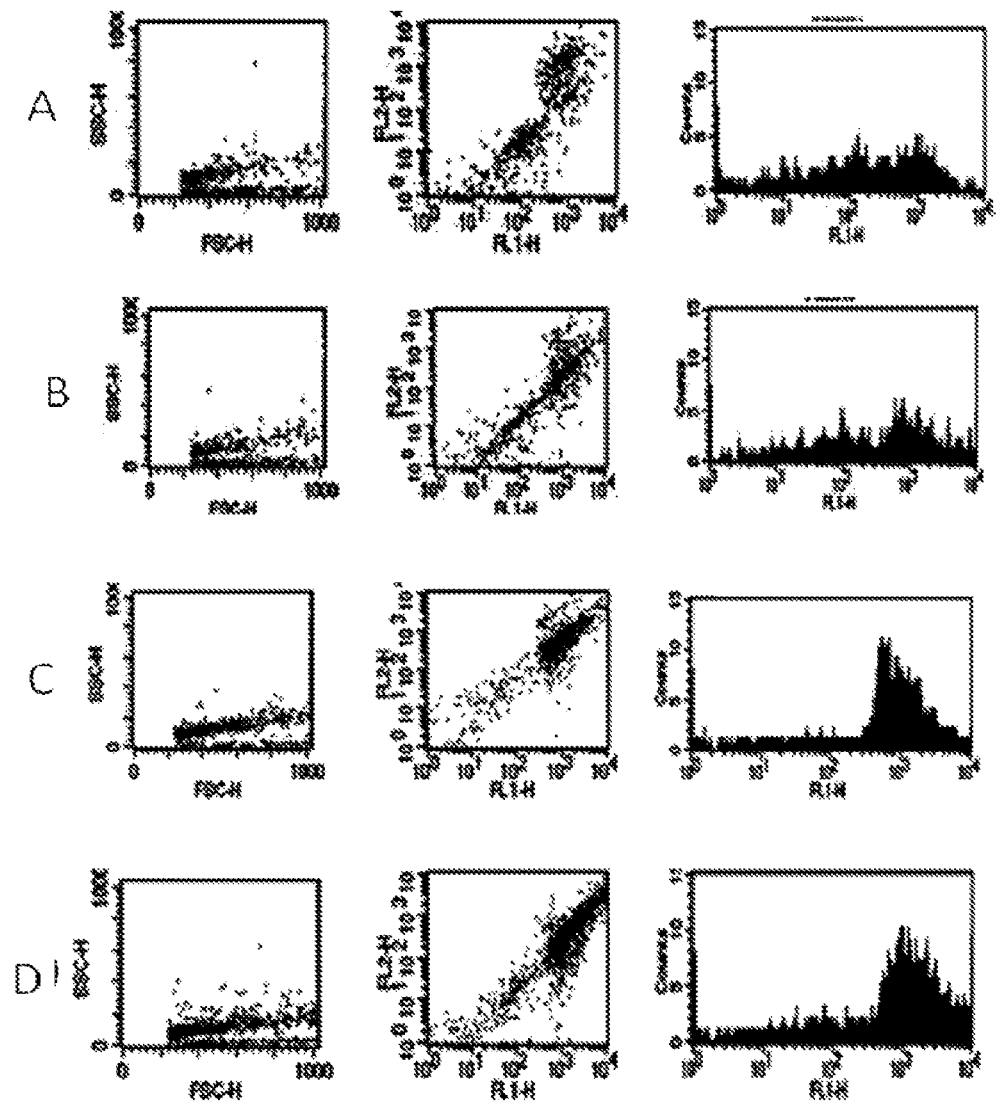
FIGS. 3A and 3B (A,B,C,D,E,F,G,H) demonstrates a non-enzymatic mechanism of ovastatin in modulating lipid particles formation.

Non-enzymatic mechanism of Ovastatin mediated cholesterol particles formation: In the second step to probe the mechanism of statin on modulating lipid particles formation, cholesterol aggregates were incubated with increasing doses of ovastatin in PBS buffer. Interestingly, compared to control experiment containing only cholesterol aggregates (FIG. 3A), it was observed that cholesterol aggregates incubated with ovastatin (1:1 and 1:2 ratios) showed a significant increase in the formation of HC-Chl and reduced LC-Chl particles (FIGS. 3C and D). However, further increase in the doses of ovastatin (1:4 and 1:16 ratios) caused formation LC-Chl and very low complex VLC-Chl cholesterol particles (FIGS. 3E, F, G).

In the negative control experiment containing only ovastatin in PBS without cholesterol aggregates no significant particles were detected in fluorescence dot plot and a few particles were detected in acquisition dot plot (FIG. 3H). This result strongly indicates that ovastatin directly induces HC-Chl particles formation in an optimum ratio with cholesterol aggregates whereas higher doses of ovastatin cause degradation or formation of LC and VLC-Chl particles formation. The degradation of lipid particles in the presence of higher doses of statins may be due to multiple mechanisms including oxidation process that cause formation of harmful free lipid radical molecules or particles. Importantly, since the assay was performed in PBS buffer without addition of any biological molecules the results clearly indicate that ovastain directly mediate LC and HC-Chl particles formation by a non-enzymatic mechanism of action. It is possible that this novel mechanism of action takes place due to interaction between lipid and ovastatin aggregates leading to the formation of statin-lipid/cholesterol complexes or particles.

Figure 3B:
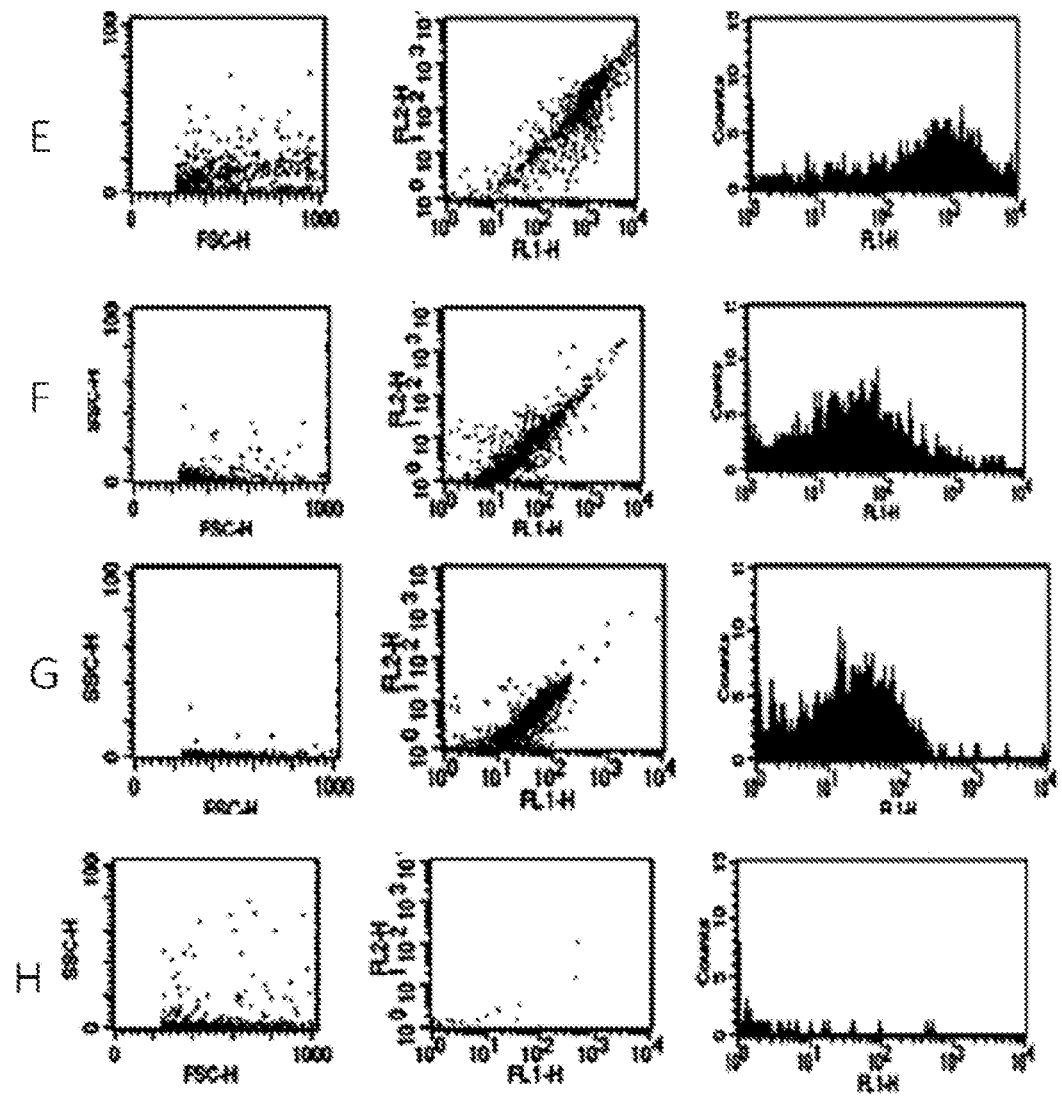

FIGS. 3A and 3B, Demonstration of non-enzymatic mechanism of ovastatin in modulating lipid particle formation. Fixed cholesterol (5 µM) versus increased doses of ovastatin (5 to 80 µM). Row A—cholesterol particles formation in the absence of statin; Left, acquisition dot plot analysis of cholesterol plaque particles; Row A—Middle, fluorescence positive cholesterol particles, Row A—Right, histogram plot showing LC-Chl and HC-Chl particles. Row B—Ovastatin (0.5:1 cholesterol ratio) induced Cholesterol particles formation, Left, acquisition dot plot analysis of cholesterol plaque particles; Row B—Middle, Ovastatin (0.5:1 cholesterol ratio) induced fluorescence cholesterol particles, Row B—Right, histogram plot showing LC-Chl and HC-Chl particles. Row C—Ovastatin (1:1 cholesterol ratio) induced Cholesterol particles formation, Left, acquisition dot plot analysis of cholesterol plaque particles; Row C—Middle, Ovastatin (1:1 cholesterol ratio) induced fluorescence cholesterol particles, Row C—Right, histogram plot showing LC-Chl and HC-Chl particles. Row D—Ovastatin (2:1 cholesterol ratio) induced Cholesterol particles formation, Left, acquisition dot plot analysis of cholesterol plaque particles; Row D—Middle, Ovastatin (2:1 cholesterol ratio) induced fluorescence cholesterol particles, Row D—Right, histogram plot showing LC-Chl and HC-Chl particles. Row E—Ovastatin (4:1 cholesterol ratio) induced Cholesterol particles formation, Left, acquisition dot plot analysis of cholesterol plaque particles; Row E—Middle, Ovastatin (4:1 cholesterol ratio) induced fluorescence cholesterol particles, Row E—Right, histogram plot showing LC-Chl and HC-Chl particles. Row F—Ovastatin (8:1 cholesterol ratio) induced Cholesterol particles formation, Left, acquisition dot plot analysis of cholesterol plaque particles; Row F—Middle, Ovastatin (8:1 cholesterol ratio) induced fluorescence cholesterol particles, Row F—Right, histogram plot showing LC-Chl and HC-Chl particles. Row G—Ovastatin (16:1 cholesterol ratio) induced Cholesterol particles formation, Left, acquisition dot plot analysis of cholesterol plaque particles; Row G—Middle, Ovastatin (16:1 cholesterol ratio) induced fluorescence cholesterol particles, Row G Right, histogram plot showing LC-Chl and HC-Chl particles. Row H—Negative control, Ovastatin only no cholesterol, Left, acquisition dot plot analysis of ovastatin; Row H—Middle, Ovastatin in fluorescence plot, Row H—Right, histogram plot showing ovastatin. This technology is conducive to testing any lipid modulating drug. Any lipid particle such as is at least one of a total cholesterol particles, total triglycerides, LDL, HDL, non-HDL lipid, combination thereof solution, or it could be biofluids such as serum or plasma, or others. This can be used for evaluating an anti-atherosclerosis drug efficacy in a pre-clinical animal model as it can be performed in vivo and detected in vitro using Flow cytometer, Nuclear Magnetic Resonance, ultra-centrifugation, ion mobility, gradient gel electrophoresis, fluorescence particle detectors and colorimetric method. A florescence label needs to be used for flow cytometer.

Figure 4:
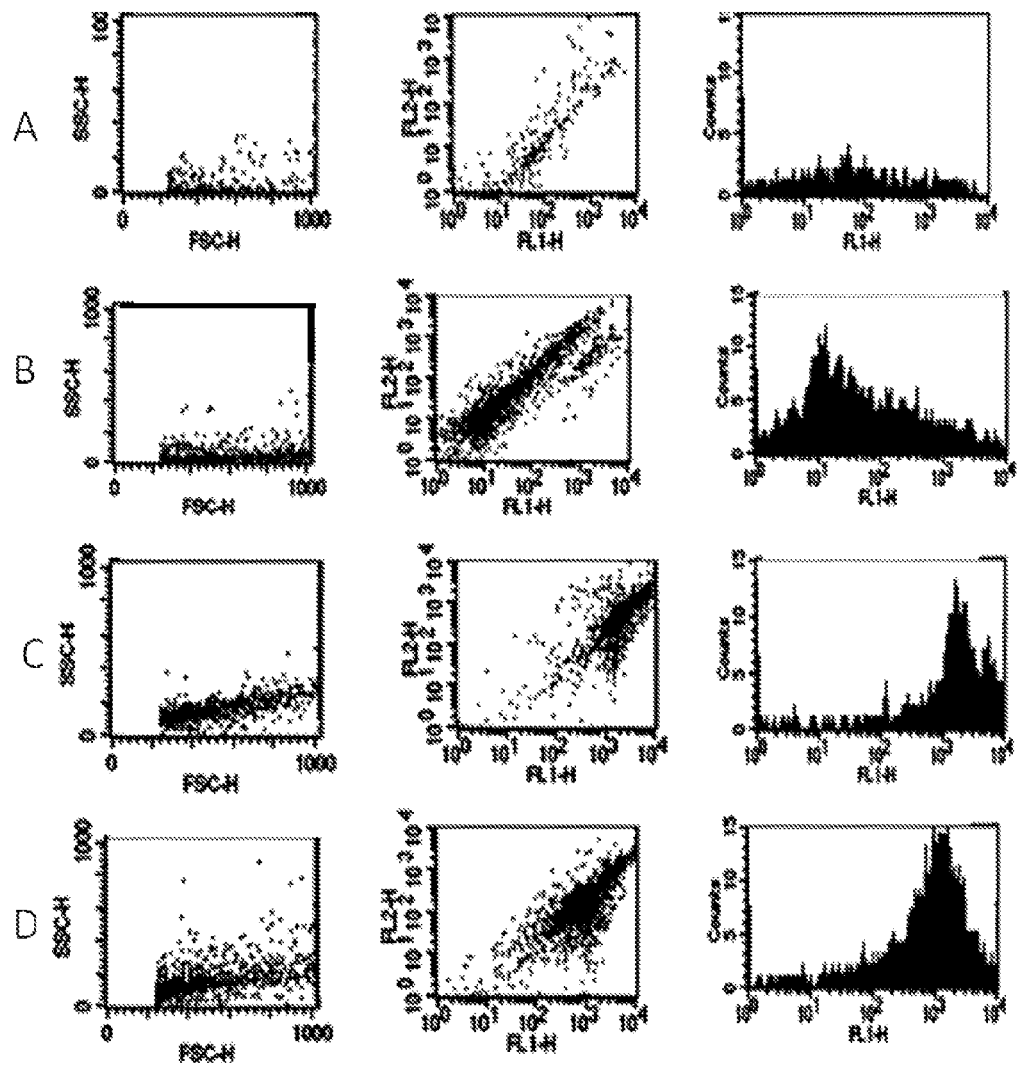
FIG. 4 (A,B,C,D) demonstrates a non-enzymatic mechanism of ovastatin in modulating phospholipid particles formation.

Ovastatin induced phospholipids particles formation: Next, effect of ovastatin on phospholipid particles formation was examined. Aggregates of fluorescence phospholipids were incubated with increasing doses of ovastatin for examination of phospholipid particles formation. The results show a dose dependent increase in high complex phospholipid (HC-Pls) particles formation (FIG. 4). Together, these results confirm that ovastatin can directly regulate lipid particles formation in a dose dependent process.

FIG. 4, Demonstration of non-enzymatic mechanism of ovastatin in modulating phospholipid particles formation. Fixed phospholipids (5 µM) versus increased doses of ovastatin (5 to 40 µM). Row A—phospholipid particles formation in the absence of statin; Left, acquisition dot plot analysis of phospholipid plaque particles; Row A—Middle, fluorescence positive phospholipid particles, Row A—Right, histogram plot showing LC-Pls and HC-Pls particles. Row B—Ovastatin (0.5:1 phospholipid ratio) induced phospholipid particles formation, Left, acquisition dot plot analysis of phospholipid plaque particles; Row B—Middle, Ovastatin (0.5:1 phospholipid ratio) induced fluorescence phospholipid particles, Row B—Right, histogram plot showing LC-Pls and HC-Pls particles. Row C—Ovastatin (1:1 phospholipid ratio) induced phospholipid particles formation, Left, acquisition dot plot analysis of phospholipid plaque particles; Row C—Middle, Ovastatin (1:1 phospholipid ratio) induced fluorescence phospholipid particles, Row C—Right, histogram plot showing LC-Pls and HC-Pls particles. Row D—Ovastatin (2:1 phospholipid ratio) induced phospholipid particles formation, Left, acquisition dot plot analysis of phospholipid plaque particles; Row D—Middle, Ovastatin (2:1 phospholipid ratio) induced fluorescence phospholipid particles, Row D—Right, histogram plot showing LC-Pls and HC-Pls particles.

Simvastatin induced cholesterol particles formation: Next, to further understand the non-enzymatic mechanism of statins, cholesterol aggregates were incubated with increasing doses of simvastatin in PBS buffer. As observed with ovastatin, cholesterol aggregates incubated with simvastatin (1:1 and 1:2 ratios) showed significant increase in HC-Chl particles formation and reduction in LC-Chl particles formation (FIGS. 5B, C and D). However, further increase in the simvastatin dose (1:4 and 1:8 ratios) led to degradation of cholesterol particles (FIG. 5E). This result further confirms the non-enzymatic mechanism of statins in modulating cholesterol particles in a dose dependent process.

Figure 5A:
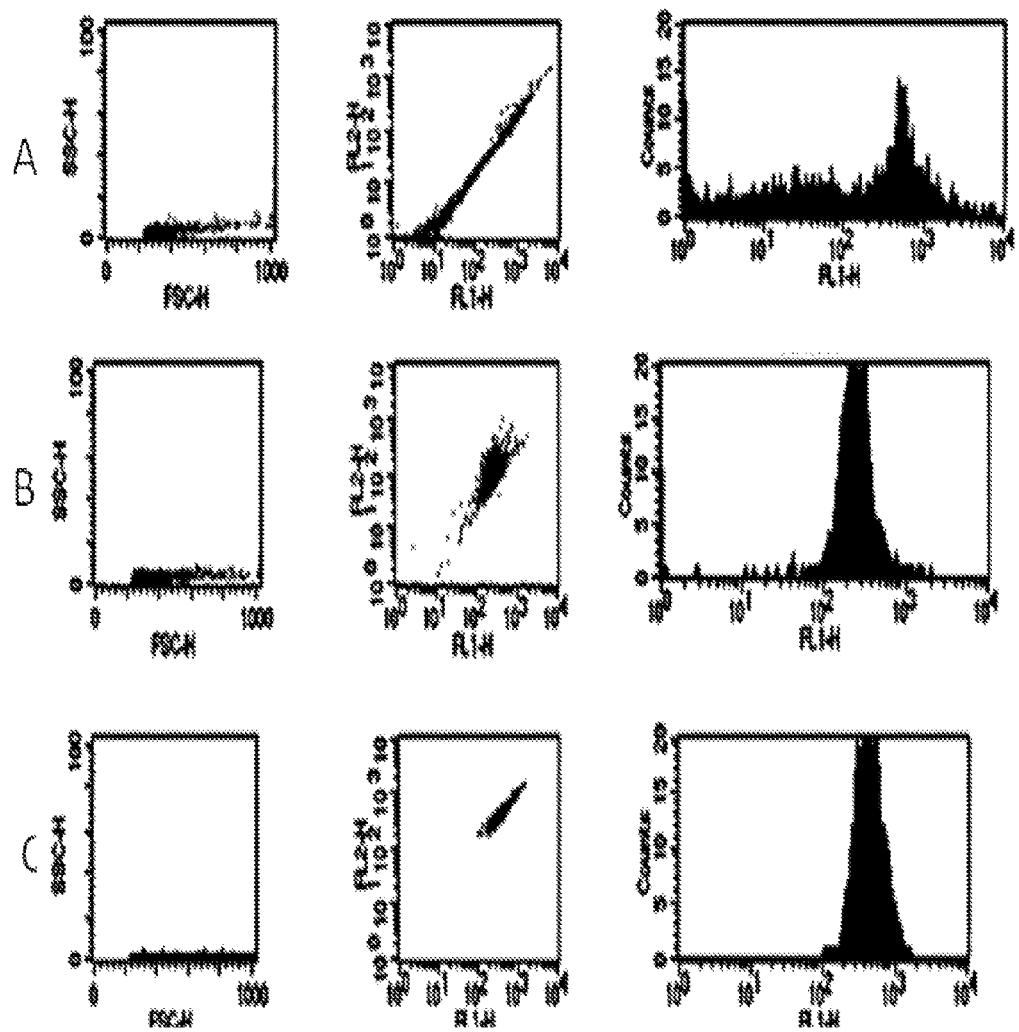
FIGS. 5A and 5B (A,B,C,D,E) demonstrates a non-enzymatic mechanism of Simvastatin.
Figure 5B:
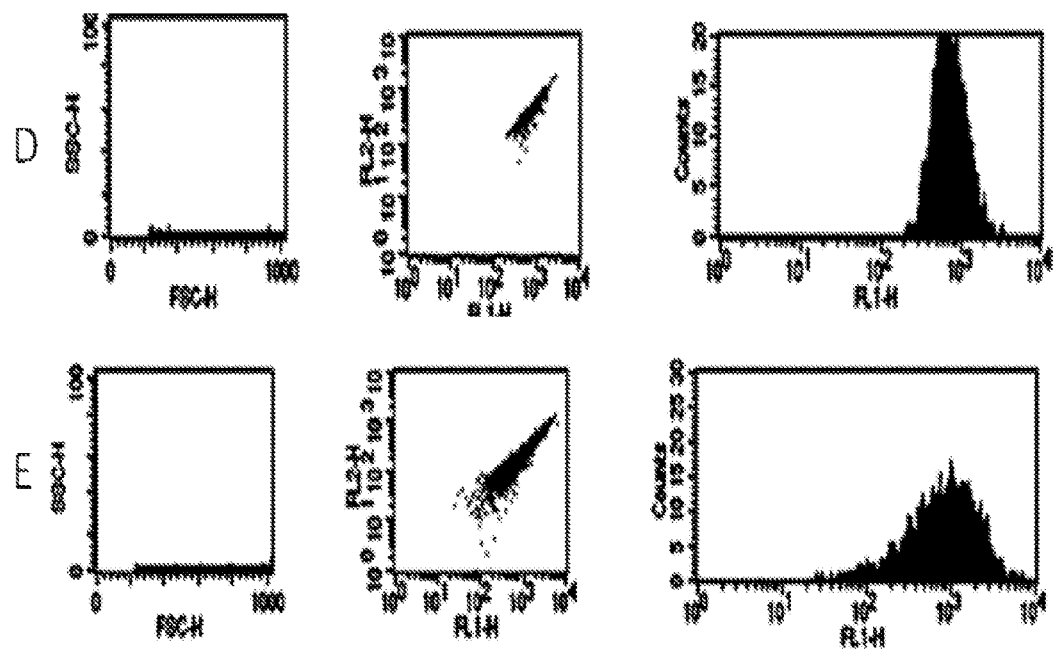

FIGS. 5A and 5B, Demonstration of a non-enzymatic mechanism of Simvastatin. Fixed cholesterol (5 µM) versus increased doses of Simvastatin (5 to 80 µM). Row A—cholesterol particles formation in the absence of statin; Left, acquisition dot plot analysis of cholesterol plaque particles; Row A—Middle, fluorescence positive cholesterol particles, Row A—Right, histogram plot showing LC-Chl and HC-Chl particles. Row B—Simvastatin (0.5:1 cholesterol ratio) induced Cholesterol particles formation, Left, acquisition dot plot analysis of cholesterol plaque particles; Row B—Middle, Simvastatin (0.5:1 cholesterol ratio) induced fluorescence cholesterol particles, Row B—Right, histogram plot showing LC-Chl and HC-Chl particles. Row C—Simvastatin (1:1 cholesterol ratio) induced Cholesterol particles formation, Left, acquisition dot plot analysis of cholesterol plaque particles; Row C—Middle, Simvastatin (1:1 cholesterol ratio) induced fluorescence cholesterol particles, Row C—Right, histogram plot showing LC-Chl and HC-Chl particles. Row D—Simvastatin (2:1 cholesterol ratio) induced Cholesterol particles formation, Left, acquisition dot plot analysis of cholesterol plaque particles; Row D—Middle, Simvastatin (2:1 cholesterol ratio) induced fluorescence cholesterol particles, Row D—Right, histogram plot showing LC-Chl and HC-Chl particles. Row E—Simvastatin (4:1 cholesterol ratio) induced Cholesterol particles formation, Left, acquisition dot plot analysis of cholesterol plaque particles; Row E—Middle, Simvastatin (4:1 cholesterol ratio) induced fluorescence cholesterol particles, Row E—Right, histogram plot showing LC-Chl and HC-Chl particles.

Figure 6:
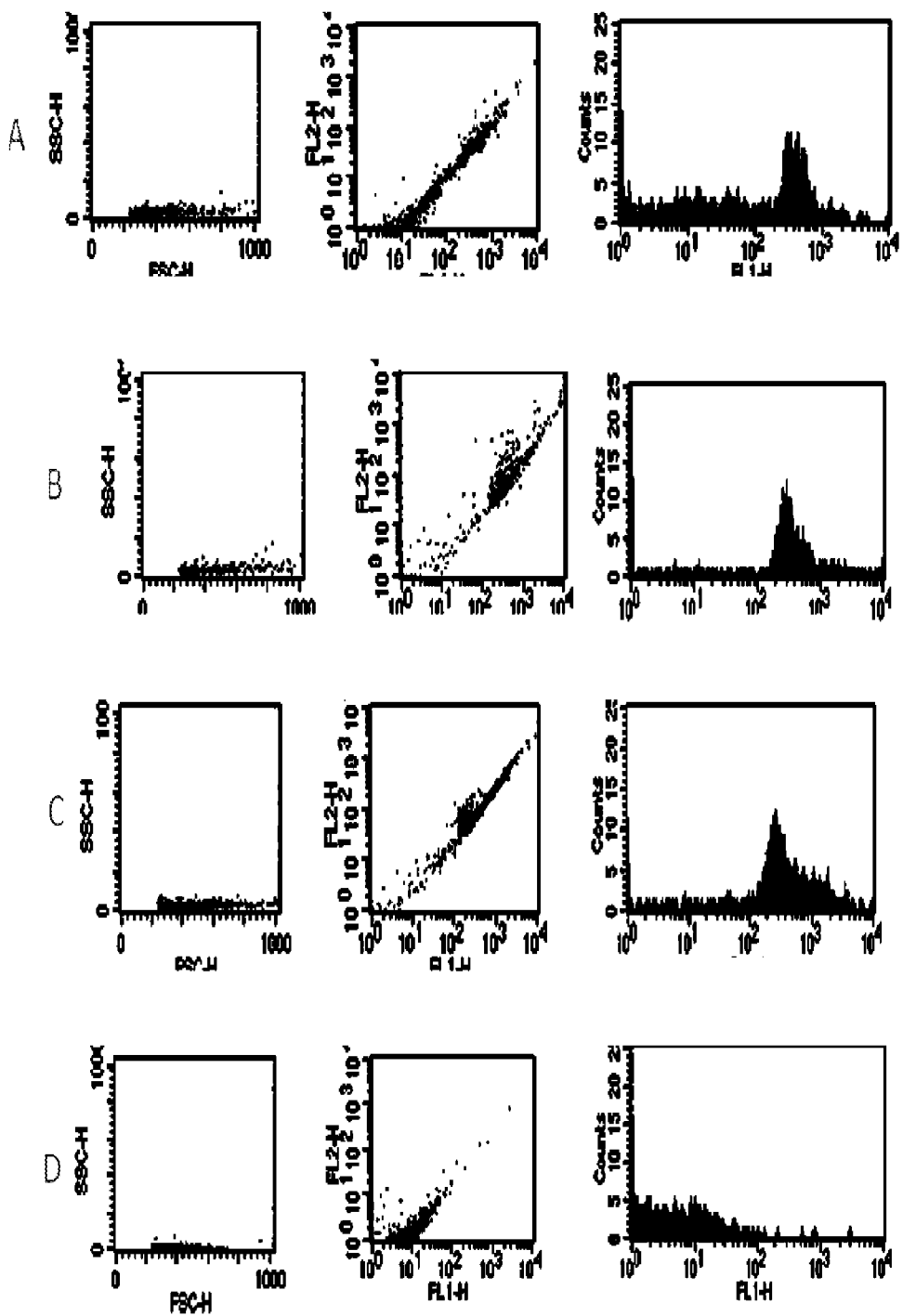
FIG. 6 (A,B,C,D) demonstrates of a non-enzymatic mechanism of Atorvastatin induced cholesterol particles formation.

Non-enzymatic mechanism of Atorvastatin induced cholesterol particles formation: Next, to further understand this novel mechanism of statin, cholesterol aggregates were incubated with increasing doses of atorvastatin in PBS buffer. As observed with ovastatin and simvastatin, cholesterol aggregates incubated with atorvastatin (1:1 to 1:4 ratios) showed a moderate level of increase in HC-Chl particles (FIG. 6 (A, B, C, D). However, further increase in the atorvastatin dose (1:8 ratios) led to degradation of cholesterol particles showing LC-Chl and VLC-Chl particles (FIG. 6k). This result further confirms the role of non-enzymatic mechanism of statins in modulating cholesterol particles.

FIG. 6, Demonstration of non-enzymatic mechanism of Atorvastatin. Fixed cholesterol (5 µM) versus increased doses of Atorvastatin (5 to 80 µM). Row A—cholesterol particles formation in the absence of statin; Left, acquisition dot plot analysis of cholesterol plaque particles; Row A—Middle, fluorescence positive cholesterol particles, Row A- Right, histogram plot showing LC-Chl and HC-Chl particles. Row B—Atorvastatin (0.5:1 cholesterol ratio) induced Cholesterol particles formation, Left, acquisition dot plot analysis of cholesterol plaque particles; Row B—Middle, Atorvastatin (0.5:1 cholesterol ratio) induced fluorescence cholesterol particles, Row B—Right, histogram plot showing LC-Chl and HC-Chl particles. Row C—Atorvastatin (1:1 cholesterol ratio) induced Cholesterol particles formation, Left, acquisition dot plot analysis of cholesterol plaque particles; Row C—Middle, Atorvastatin (1:1 cholesterol ratio) induced fluorescence cholesterol particles, Row C—Right, histogram plot showing LC-Chl and HC-Chl particles. Row D—Atorvastatin (2:1 cholesterol ratio) induced Cholesterol particles formation, Left, acquisition dot plot analysis of cholesterol plaque particles; Row D—Middle, Atorvastatin (2:1 cholesterol ratio) induced fluorescence cholesterol particles, Row D—Right, histogram plot showing LC-Chl and HC-Chl particles.

Figure 7A:
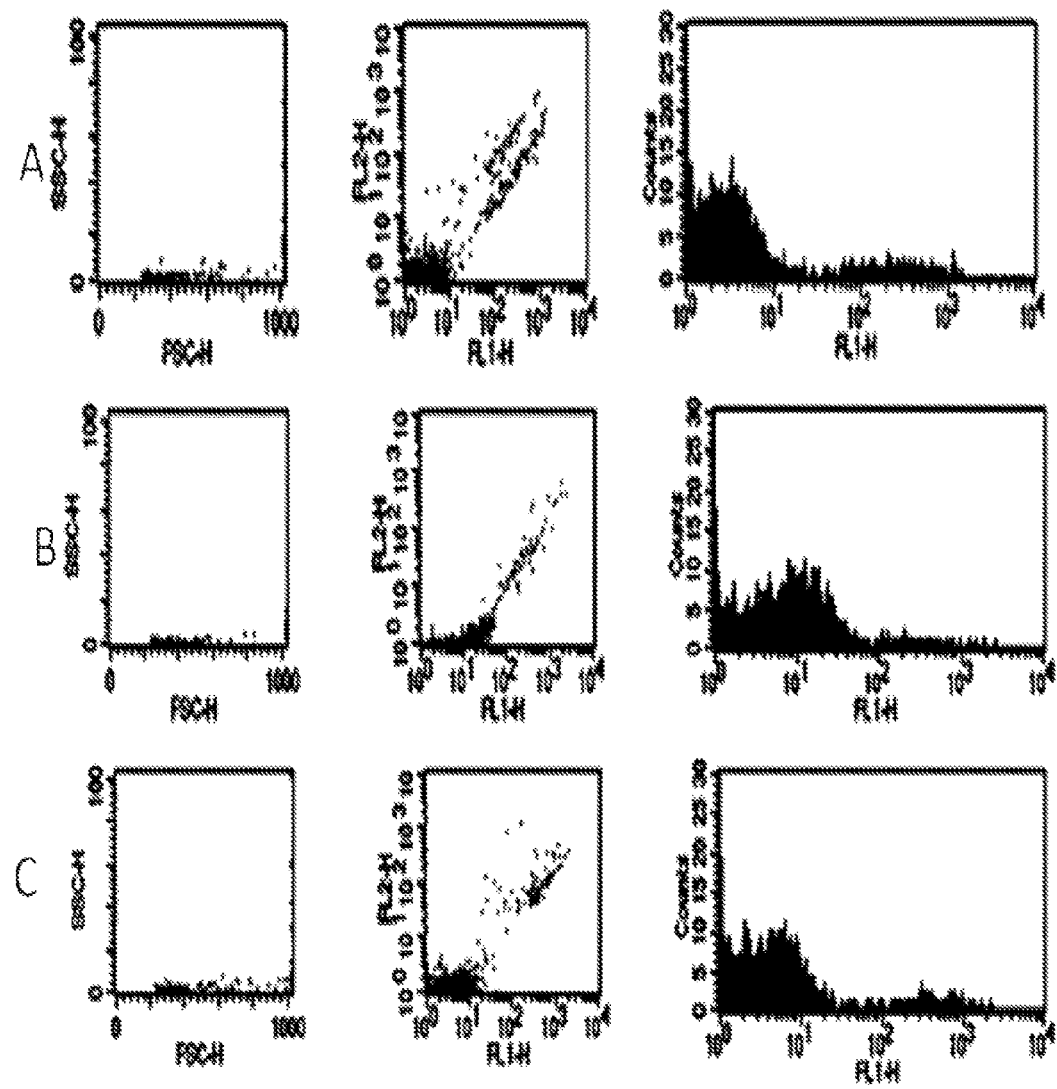
FIGS. 7A and 7B (A,B,C,D,E) shows analysis and effect of Fluvastatin on cholesterol particles formation.
Figure 7B:
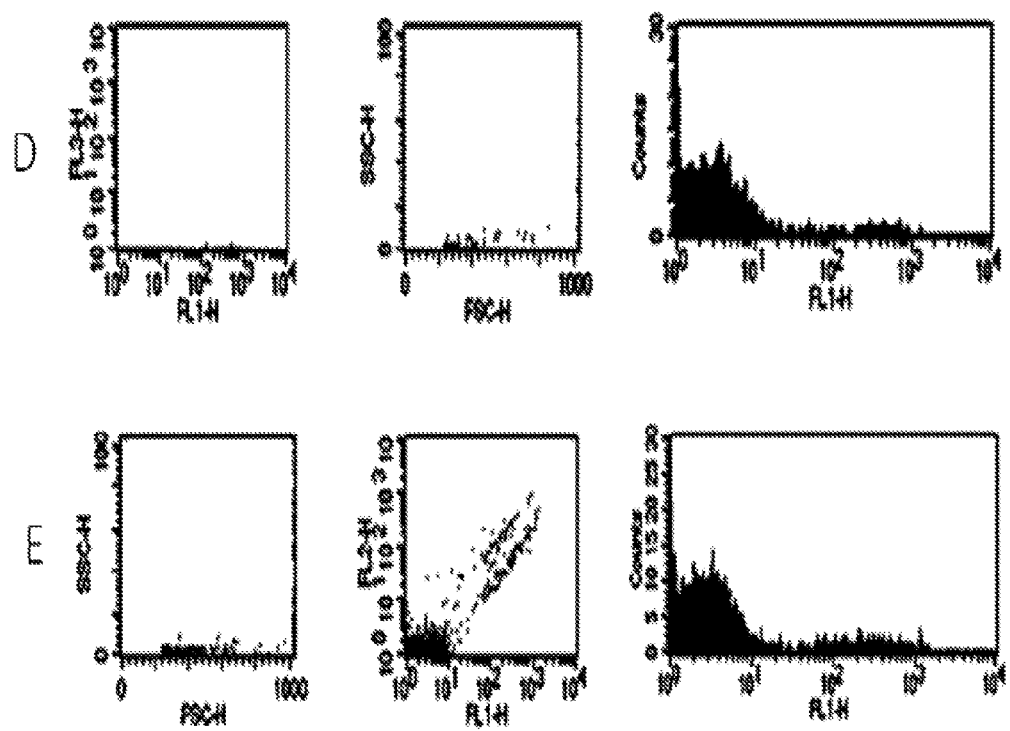

Analyzing effect of Fluvastatin on cholesterol particles formation: In the aforementioned experiments lipophilic statins such as ovastatin, sumastatin and atorvastatin were used to examine their effects on lipid particles formation. Next, fluvastatin, a hydrophilic statin, was used for incubation with cholesterol aggregates. As performed earlier with other statins, cholesterol aggregates were incubated with increasing concentrations of fluvastatin in PBS buffer. In contrast to other statins used in this study, fluvastatin even at the higher dose level (1:8 ratio) did not alter the LC-Chl and HC-Chl particles formation (FIGS. 7A and 7B). These results suggest variations among statins in exhibiting non-enzymatic mechanism of action. FIGS. 7A and 7B, Demonstration of non-enzymatic mechanism of Fluvastatin. Fixed cholesterol (5 µM) versus increased doses of Fluvastatin (5 to 80 µM). Row A—cholesterol particles formation in the absence of statin; Left, acquisition dot plot analysis of cholesterol plaque particles; Row A—Middle, fluorescence positive cholesterol particles, Row A—Right, histogram plot showing LC-Chl and HC-Chl particles. Row B—Fluvastatin (0.5:1 cholesterol ratio) induced Cholesterol particles formation, Left, acquisition dot plot analysis of cholesterol plaque particles; Row B—Middle, Fluvastatin (0.5:1 cholesterol ratio) induced fluorescence cholesterol particles, Row B—Right, histogram plot showing LC-Chl and HC-Chl particles. Row C—Fluvastatin (1:1 cholesterol ratio) induced Cholesterol particles formation, Left, acquisition dot plot analysis of cholesterol plaque particles; Row C—Middle, Fluvastatin (1:1 cholesterol ratio) induced fluorescence cholesterol particles, Row C—Right, histogram plot LC-Chl and HC-Chl particles. Row D—Fluvastatin (2:1 cholesterol ratio) induced Cholesterol particles formation, Left, acquisition dot plot analysis of cholesterol plaque particles; Row D—Middle, Fluvastatin (2:1 cholesterol ratio) induced fluorescence cholesterol particles, Row D—Right, histogram plot showing LC-Chl and HC-Chl particles. Row E—Fluvastatin (4:1 cholesterol ratio) induced Cholesterol particles formation, Left, acquisition dot plot analysis of cholesterol plaque particles; Row E—Middle, Fluvastatin (4:1 cholesterol ratio) induced fluorescence cholesterol particles, Row E—Right, histogram plot showing LC-Chl and HC-Chl particles. Since many examples are shown that the assay or the method modulates the lipid particle in one way or the other, use this lipid particle profile to make a new lipid modulating drug is not only be dome but it is novel.

A big issue about individual variations to drugs had dogged the industry to prescribe and make one size fits all lipid modulating drugs with a lot of side effects. These assay and methods described herein enables to use the lipid particle profile on the effect of the statin drug to the lipid aggregate and modulating a treatment for a patient. Some of these are important to observe because even if the lipid lowering drug is effective a higher dose is counter effective. Please see FIG. 3B, row G for the effect of statin in increasing the LD—cholesterol particle. This novel assay or method enables the user not only to modulate the lipid particles but also the drug dosage to determine the efficacious drug making strategy and also may be combination therapy that best suits the patients.

Figure 8:
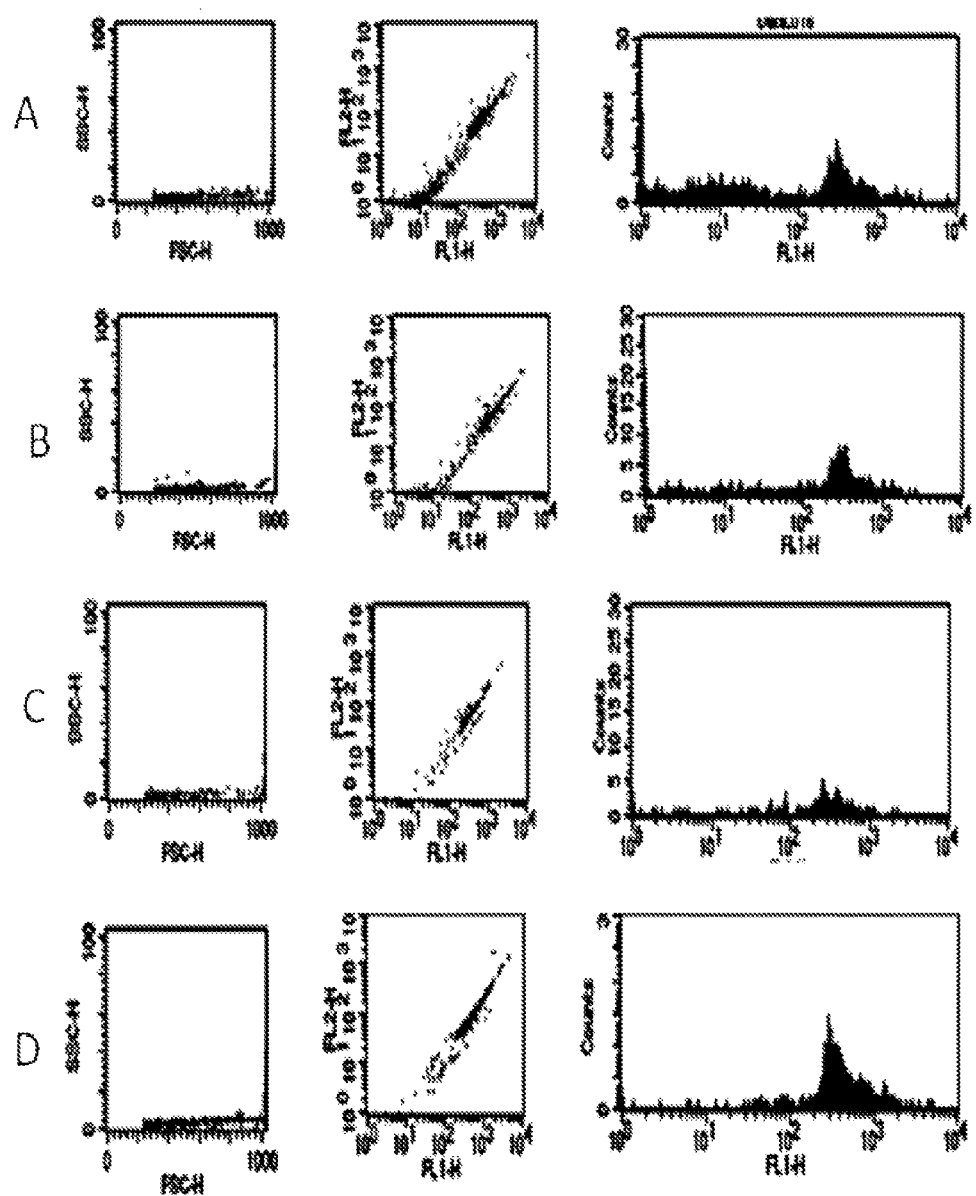
FIG. 8 (A,B,C,D) demonstrates non-enzymatic mechanism of Pravastatin.

Pravastatin mediated cholesterol particles formation: Next, cholesterol aggregates were incubated with increasing doses of pravastatin in PBS buffer. The results show only a low level of pravastatin effect in altering the profile of LC-Chl and HC-Chl particles formation (FIG. 8). FIG. 8, Demonstration of non-enzymatic mechanism of Pravastatin. Fixed cholesterol (5 µM) versus increased concentration of Pravastatin (5 to 80 µM). Row A—cholesterol particles formation in the absence of statin; Left, acquisition dot plot analysis of cholesterol plaque particles; Row A—Middle, fluorescence positive cholesterol particles, Row A—Right, histogram plot showing LC-Chl and HC-Chl particles. Row B—Pravastatin (0.5:1 cholesterol ratio) induced Cholesterol particles formation, Left, acquisition dot plot analysis of cholesterol plaque particles; Row B—Middle, Pravastatin (0.5:1 cholesterol ratio) induced fluorescence cholesterol particles, Row B—Right, histogram plot showing LC-Chl and HC-Chl particles. Row C—Pravastatin (1:1 cholesterol ratio) induced Cholesterol particles formation, Left, acquisition dot plot analysis of cholesterol plaque particles; Row C—Middle, Pravastatin (1:1 cholesterol ratio) induced fluorescence cholesterol particles, Row C—Right, histogram plot showing LC-Chl and HC-Chl particles. Row D—Pravastatin (2:1 cholesterol ratio) induced Cholesterol particles formation, Left, acquisition dot plot analysis of cholesterol plaque particles; Row D—Middle, Pravastatin (2:1 cholesterol ratio) induced fluorescence cholesterol particles, Row D—Right, histogram plot showing LC-Chl and HC-Chl particles.

Effect of pH on Simvastatin mediated cholesterol particles formation: Experiments with ovastatin, simvastatin and atorvastain clearly showed that lipophilic statins have significant effect on altering profiles of low complex and high complex lipid particles formation. The experiments were carried out in PBS buffer without any biomolecules present in the reaction. Next to probe the factors that may influence the non-enzymatic mechanism of statins, experiments were carried out using PBS buffer with broad range of pH (pH 3.0 to pH 9.0). Cholesterol aggregates were incubated with simvastatin in a fixed ratio of 1:2 in PBS buffer with increasing pH conditions. Interestingly, a higher level of HC-Chl particles formation was observed in pH 3.0 to pH 7.0 and no LC-Chl particles were observed suggesting elevated level of conversion of LC-Chl into HC-Chl particles (FIG. 9 (A, B and C)). Conversely, cholesterol aggregates incubated in PBS (pH 8.0) caused significant level of degradation leading to the formation of LC-Chl and VLC-Chl particles (FIG. 9(D)). This experiment reveals that non-enzymatic mechanism of statins is a pH sensitive reaction and acidic to neutral pH are favorable for statins inducing HC-Chl particles formation whereas at alkaline pH condition statin induces LC-Chl and VLC-Chl particles formation.

Figure 9:
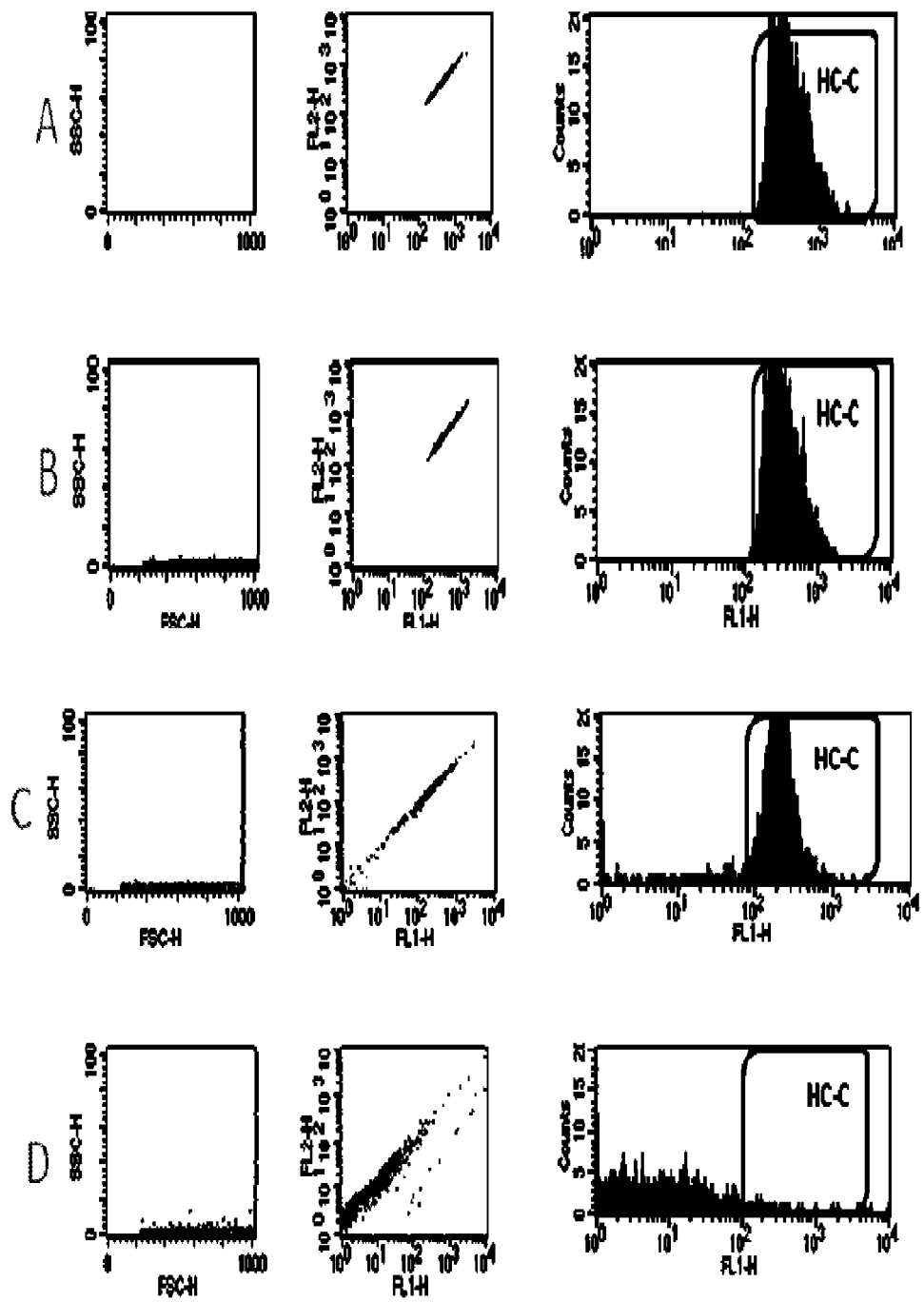
FIG. 9 (A,B,C,D) shows the effect of probing of pH on non-enzymatic mechanism of Simvastatin.

FIG. 9, Probing the effect of pH on non-enzymatic mechanism of Simvastatin. Fixed cholesterol and Simvastatin (5 µM each) versus broad range of pH (3 to 9). Row A—cholesterol particles formation in the pH 3.3; Left, acquisition dot plot analysis of cholesterol plaque particles; Row A—Middle, fluorescence positive cholesterol particles, Row A—Right, histogram plot showing LC-Chl and HC-Chl particles. Row B—cholesterol particles formation in the pH 6.3, Left, acquisition dot plot analysis of cholesterol plaque particles; Row B—Middle, fluorescence cholesterol particles. Row B—Right, histogram plot showing LC-Chl and HC-Chl particles. Row C—cholesterol particles formation in the pH 7.3, Left, acquisition dot plot analysis of cholesterol plaque particles; Row C—Middle, fluorescence cholesterol particles, Row C—Right, histogram plot showing LC-Chl and HC-Chl particles. Row D—cholesterol particles formation in the pH 8.4, Left, acquisition dot plot analysis of cholesterol plaque particles; Row D—Middle, fluorescence cholesterol particles, Row D—Right, histogram plot showing LC-Chl and HC-Chl particles.

The use of statins has revolutionized the management of CVD patients. In addition to statin-induced reductions in LDL cholesterol (LDL-C) there is increasing circumstantial evidences supporting the ability of statins to increase HDL cholesterol (HDL-C). In contrast to the reduction in LDL-C, the mechanism by which statins increase the concentration of HDL-C is not known and also magnitude of the increase in HDL-C and its relationship to dose varies widely between different statins (Barter P J et al, 2010). The above described experiments carried out between lipid aggregates and statins consistently proved that statins, in addition to enzymatic mechanism of HMG=CoA reductase inhibitor, have a non-enzymatic mechanism of action involved in the lipid particles formation. We have also found that statins exhibit variations in their effect in inducing LC-Chl and HC-Chl particles formation. Among all the statins tested simvastatin was found to have higher magnitude of effect in inducing HC-Chl particles followed by ovastatin whereas atorvastatin, rosuvastatin and pravastatin have moderate to low level of effects. Fluvastatin was found to have a little or no effect in altering LC-Chl and HC-Chl particles. Importantly, these results are in good agreement with evidences obtained from a number of statin clinical studies. For example, the meta analysis of statin clinical studies have determined the efficacy of statins in increasing HDL particles in the order of: atorvastatin, simvastatin, pravastatin, lovastatin and fluvastatin (Asztalas B F et al, 2002; Schaefer E J et al, 2004). However, the clinical significance and mechanism by which the statins inducing HDL cholesterol particles is unknown (Yun K H et al, 2013). Accordingly, comparison of our statin data with statin clinical trial data suggests the statins induced increase in HDL particles formation observed in the clinical population might be due to the non-enzymatic mechanism of statins described in this application.

Development of a statin response test using serum samples: Our conclusion that statins modulate lipid particles formation by a non-enzymatic mechanism was drawn based on the assay carried out in PBS buffer that contains no biological molecules. Hence clinical significance of statin-induced changes in low and high-density lipoprotein particles by non enzymatic mechanism needs to be evaluated in the biological fluids. Human serum/plasma is the most complex fluid among other biological fluids since they contain approximately 10,500 proteins, antibodies and other metabolites. Therefore, to determine how statins modulate serum concentrations of LC-Chl and HC-Chl particles the following experiments were carried out using serum samples.

Serially diluted serum samples (20% to 2%) were mixed with ovastatin and cholesterol aggregates/oligomers (1:1 ratio) for examining LC-Chl and HC-Chl particles formation. Flow cytometer based analysis of the resulting serum samples showed significant redistribution in LC-Chl and HC-Chl particles profile in 5% and 2% diluted serum samples (FIGS. 10C and D). As a result, this data indicates that non-enzymatic mechanism of statin works in serum samples also contributing to increase in HC-Chl particles as observed in experiments carried out using PBS buffer only.

Figure 10:
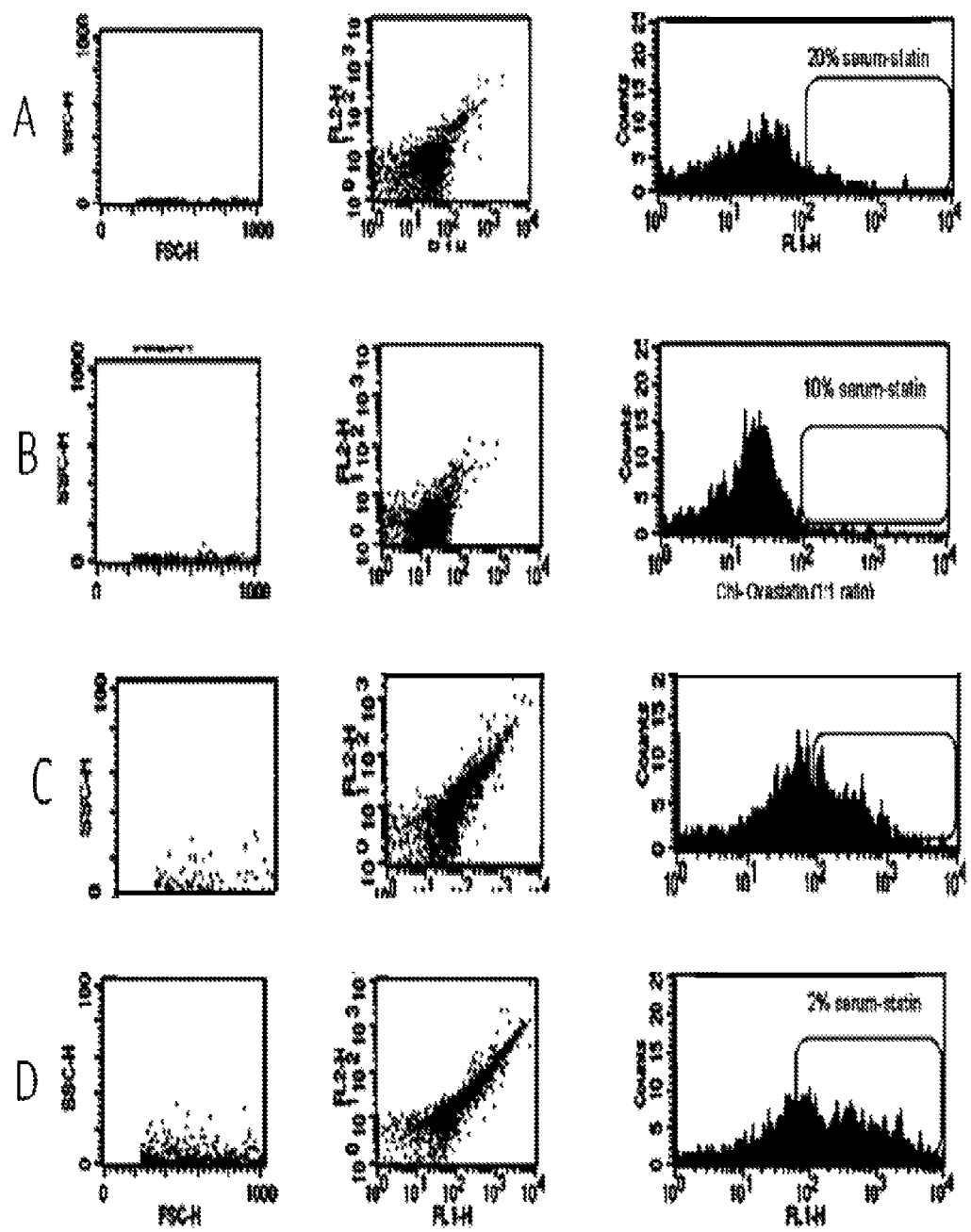
FIG. 10 (A,B,C,D) demonstrates a non-enzymatic mechanism of Ovastatin in human serum sample.

FIG. 10, Demonstration of non-enzymatic mechanism of Ovastatin in human serum sample. Fixed cholesterol and Ovastatin (5 µM each) versus diluted serum (20 to 2%). Row A—cholesterol particles formation in the 20% serum; Left, acquisition dot plot analysis of cholesterol plaque particles; Row A—Middle, fluorescence positive cholesterol particles, Row A—Right, histogram plot showing LC-Chl and HC-Chl particles. Row B—cholesterol particles formation in 10% serum, Left, acquisition dot plot analysis of cholesterol plaque particles; Row B—Middle, fluorescence cholesterol particles, Row B—Right, histogram plot showing LC-Chl and HC-Chl particles. Row C—cholesterol particles formation in 5% serum, Left, acquisition dot plot analysis of cholesterol plaque particles; Row C—Middle, fluorescence cholesterol particles, Row C—Right, histogram plot showing cholesterol (HC-Chl) particles. Row D—cholesterol particles formation in 2% serum, Left, acquisition dot plot analysis of cholesterol plaque particles; Row D—Middle, fluorescence cholesterol particles, Row D—Right, histogram plot showing cholesterol particles.

Figure 11:
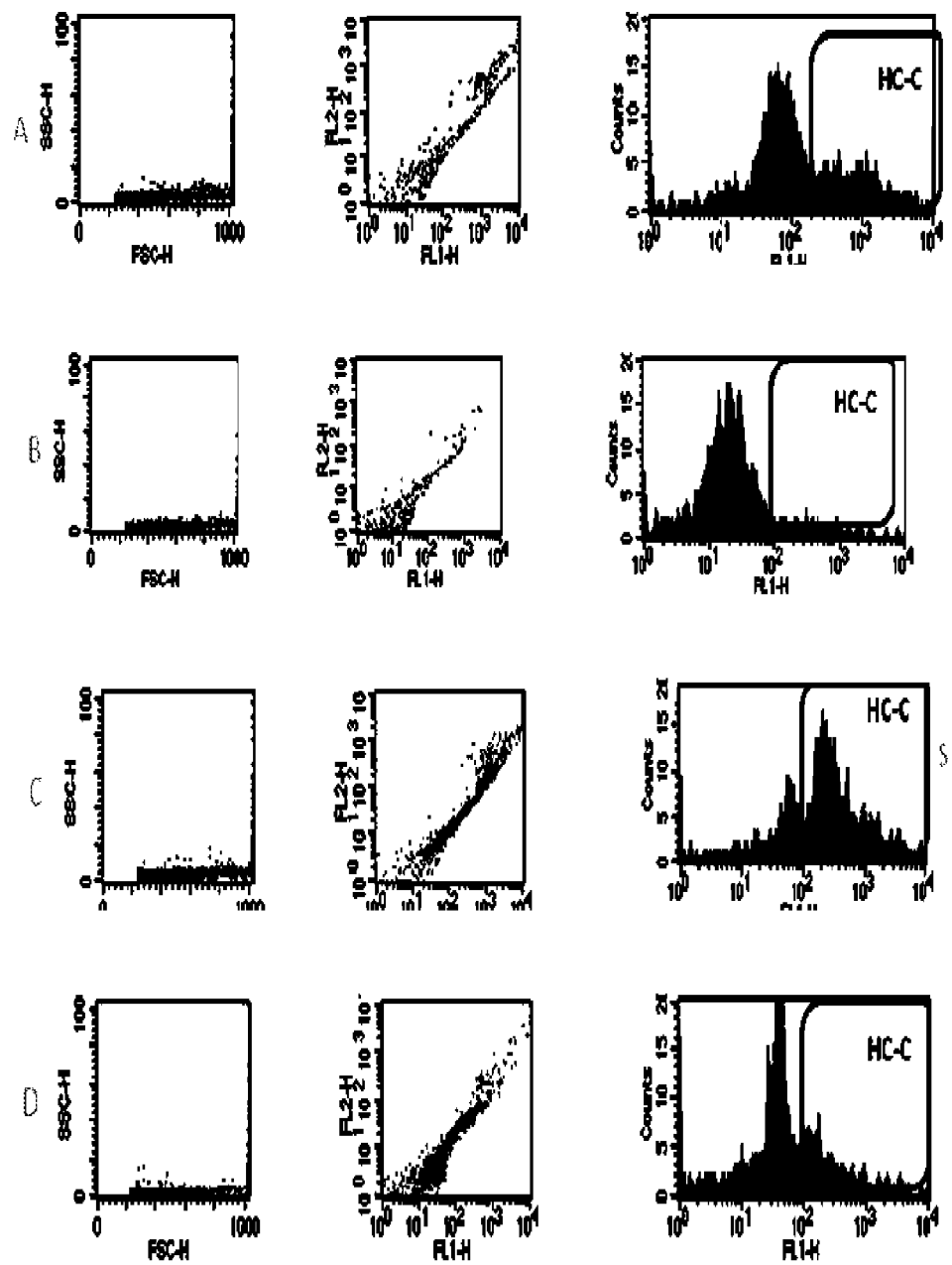
FIG. 11 (A,B,C,D) demonstrates a non-enzymatic mechanism of Simvastatin in two different (SB6 and SR9) human serum samples.

Next, to further demonstrate the functions of statin mediated non-enzymatic mechanism of action in serum sample, serially diluted serum samples (10% and 5%) were mixed with simvastatin and cholesterol aggregates/oligomers (2:1 ratio) for examining LC-Chl and HC-Chl particles formation. For correlation analysis, two serum samples obtained from atherosclerotic patients were used. Flow cytometer based analysis of the resulting serum samples showed significant redistribution in LC-Chl and HC-Chl particles profile in the 5% and 10% diluted serum samples (FIG. 11). There is clear shift in the fractions of LC-Chl to HC-Chl profile was observed. However, compared to SB6 serum sample, the effect of simvastatin induced HC-Chl particles formation in the serum sample SR9 was higher indicating variation among patients in response to simvastatin. This data further confirms functioning of non-enzymatic mechanism of action of statin in serum samples.

FIG. 11, Demonstration of non-enzymatic mechanism of Simvastatin in two different (SB6 and SR9) human serum samples. Fixed cholesterol and Simvastatin (1:2 ratio) versus diluted serum (10 and 5%). Row A—cholesterol particles formation in the 10% serum; Left, acquisition dot plot analysis of cholesterol plaque particles; Row A—Middle, fluorescence positive cholesterol particles, Row A—Right, histogram plot showing LC-Chl and HC-Chl particles. Row B—cholesterol particles formation in 5% serum, Left, acquisition dot plot analysis of cholesterol plaque particles; Row B—Middle, fluorescence cholesterol particles, Row B—Right, histogram plot showing LC-Chl and HC-Chl particles formation in 10% serum, Left, acquisition dot plot analysis of cholesterol plaque particles; Row C—Middle, fluorescence cholesterol particles, Row C—Right, histogram plot showing cholesterol (HC-Chl) particles. Row D—cholesterol particles formation in 5% serum, Left, acquisition dot plot analysis of cholesterol plaque particles; Row D—Middle, fluorescence cholesterol particles, Row D—Right, histogram plot showing cholesterol particles.

Figure 12:
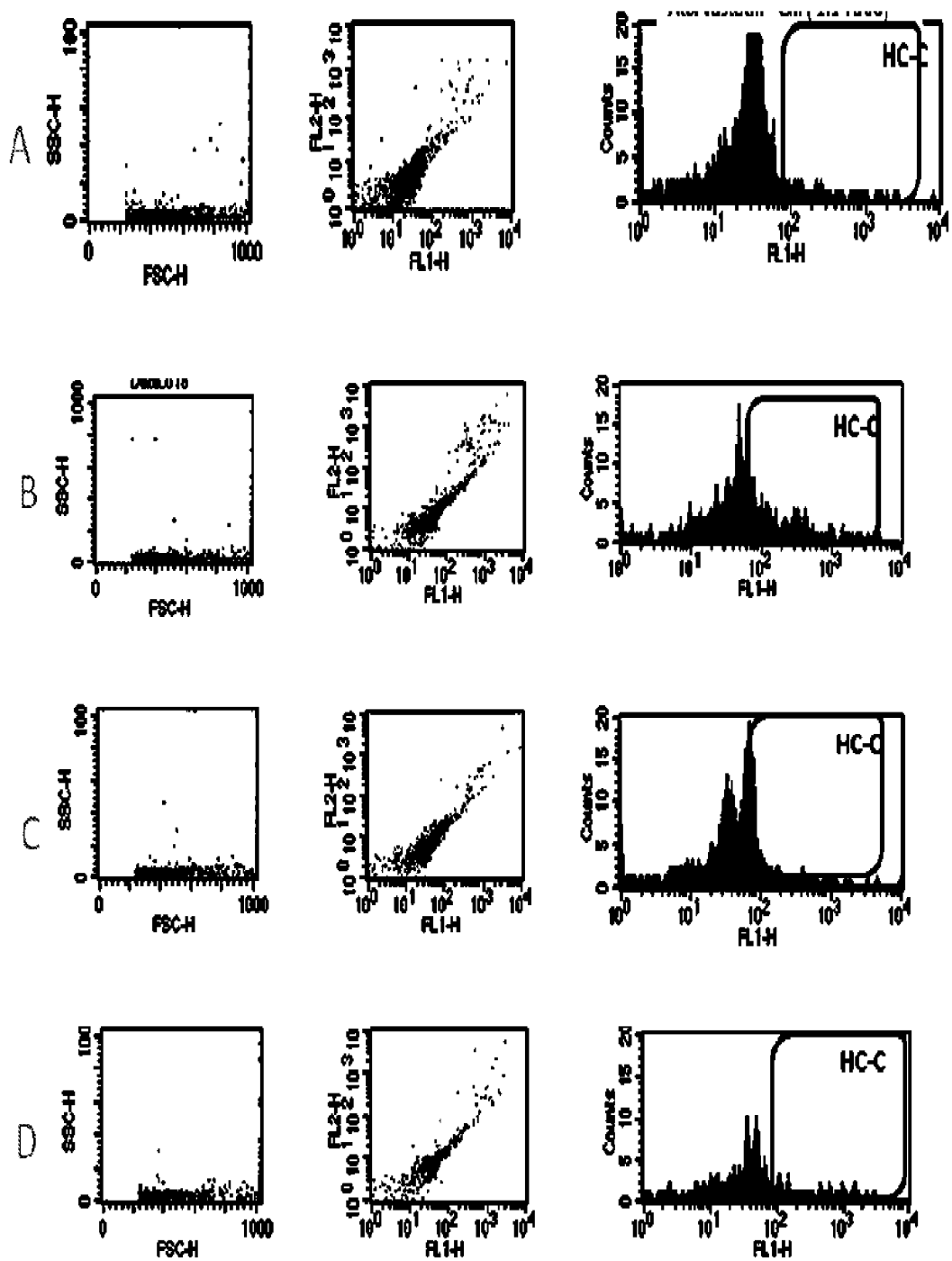
FIG. 12 (A,B,C,D) demonstrates a non-enzymatic mechanism of Atorvastatin in human serum samples

Next, to gain further evidence, the statin response test was repeated using increasing dose of atorvastatin added to diluted serum sample (5%). The atorvastatin was mixed with cholesterol aggregates/oligomers for examining LC-Chl and HC-Chl particles formation. Flow cytometer based analysis of the resulting serum samples showed dose dependent redistribution in LC-Chl and HC-Chl particles profile (FIG. 12). Taken together, the statin response test described here is a theranostic test combining both diagnosis and drug efficacy analysis in a single assay. In addition, observation of variation in the serum samples suggests additional factors/components present in the biofluids may influence this non-enzymatic mechanism. The statin response test not only helps to measure profiles of LC-Chl and HC-Chl particles but also can be used to measure total cholesterol, total triglycerides, LDL, HDL, and non-HDL cholesterol, and triglycerides in serum samples obtained from human and other animals.

FIG. 12, Demonstration of non-enzymatic mechanism of Atorvastatin in human serum samples. Fixed cholesterol (5 µM) versus increasing Atorvastatin in diluted serum (10%). Row A—cholesterol particles formation in Atorvastatin 5 µM; Left, acquisition dot plot analysis of cholesterol plaque particles; Row A—Middle, fluorescence positive cholesterol particles, Row A—Right, histogram plot showing LC-Chl and HC-Chl particles. Row B—cholesterol particles formation in 10 µM Atorvastatin, Left, acquisition dot plot analysis of cholesterol plaque particles; Row B—Middle, fluorescence cholesterol particles, Row B—Right, histogram plot showing LC—Chl and HC—Chl particles. Row C—cholesterol particles formation in 20 µM Atorvastatin, Left, acquisition dot plot analysis of cholesterol plaque particles; Row C—Middle, fluorescence cholesterol particles, Row C—Right, histogram plot showing cholesterol (HC-Chl) particles. Row D—cholesterol particles formation without Atorvastatin, Left, acquisition dot plot analysis of cholesterol plaque particles; Row D—Middle, fluorescence cholesterol particles, Row D—Right, histogram plot showing cholesterol particles.

Figure 13:
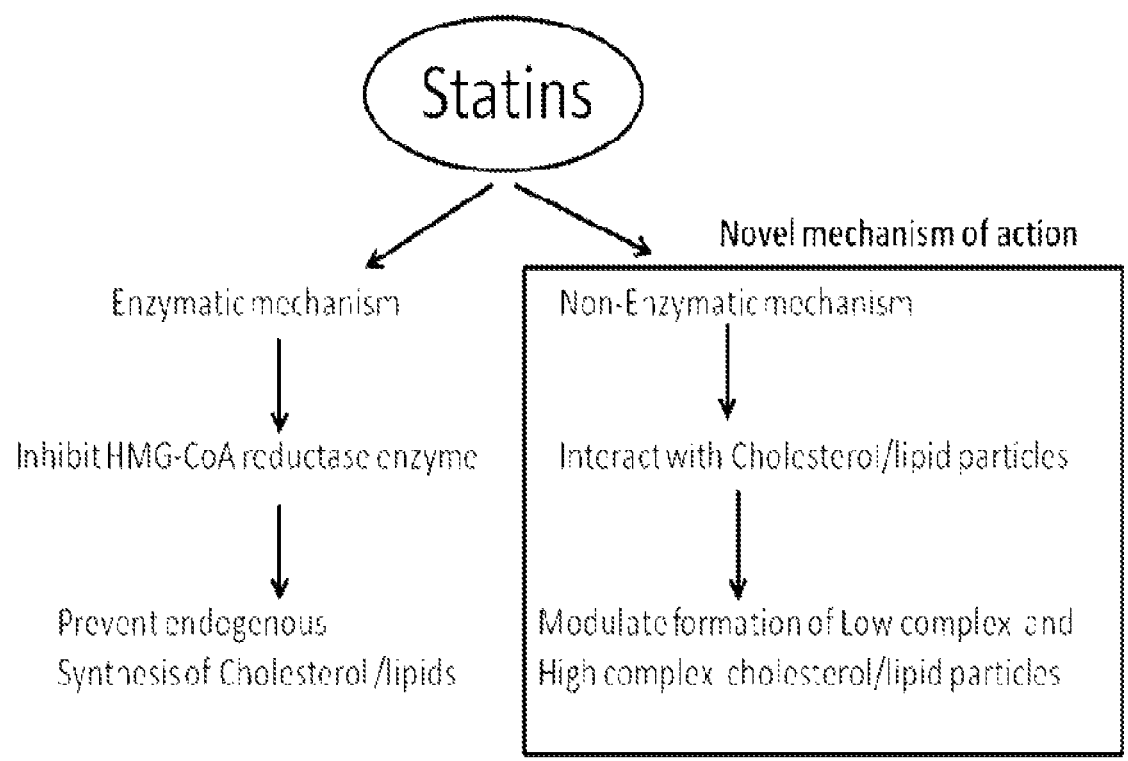
FIG. 13 shows the comparative analysis of enzymatic and non-enzymatic mechanism of statins in regulating metabolism of lipids.

Comparison of enzymatic and non-enzymatic mechanism of actions of statins: Meta-analysis of clinical studies data has shown that statins in addition to reducing LDL concentration also induce increases in HDL levels (Lüscher TF, 2014). It has been estimated that statins induced elevation of HDL-C ranges between 3% to 15%. Besides, all statins to a greater or lesser degree, have the potential to cause adverse events if administered in high doses or in combination with other medications (Macedo A et al, 2014). In conclusion, the novel mechanism disclosed herein strongly indicates that statins, in addition to inhibiting de novo cholesterol synthesis via HMG-CoA enzyme mechanism, can regulate cholesterol particles formation by a non-enzymatic mechanism (FIG. 13). The enzymatic mechanism of statin is known to inhibit endogenous cell mediated cholesterol synthesis whereas the non-enzymatic mechanism disclosed herein may play important for modulating lipid particles formation in a post cholesterol synthesis state or cholesterol absorbed from exogenous food sources. Accordingly, the theranostic approach based statin response test disclosed in this application is a simple, accurate and mechanism based assay that helps to determine effect of statins on LDL and HDL lipids/cholesterol particles formation. In addition, this test allows early screening of patients to identify right statin and dose ranges thereby mitigate potential sides effects associated with statin therapy. FIG. 13 depict comparative analysis of enzymatic and non-enzymatic mechanism of statins in regulating metabolism of lipids.

Figure 14:
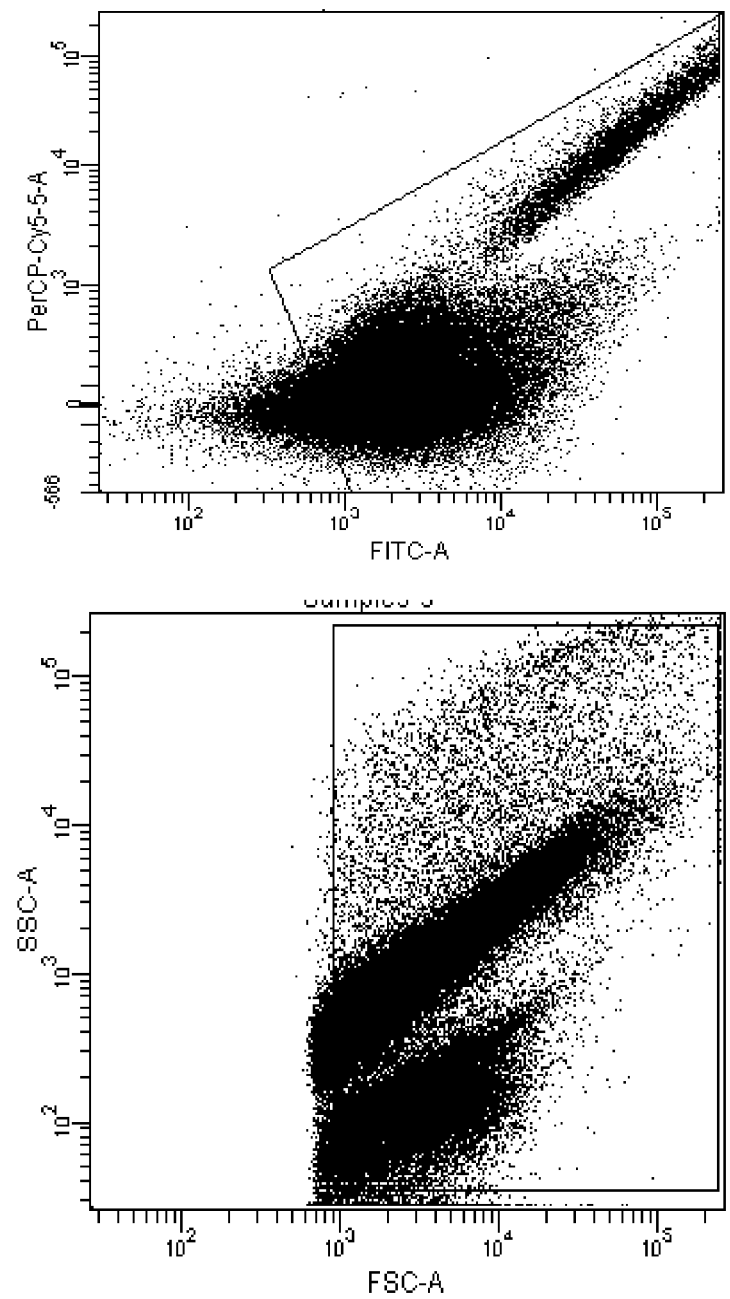
FIG. 14 shows the Flow cytometer assessment and sorter-based isolation of statin induced cholesterol particles.

Proteomics analysis of statin induced cholesterol particles: The statin response test developed using serum samples showed that ovastatin, simvastatin and atorvastatin induce HC-Chl particles formation. It was also observed that statins induce clear shift in the profile of LC-Chl concentration indicating rearrange of cholesterol particles size and their compositions. This result is supported by earlier clinical studies demonstrating statin induced modification of HDL metabolism and reverse cholesterol transport mechanism (Arsenault B J and Boekholdt S M, 2014). Previously we have reported that cholesterol aggregates incubated in the serum samples are converted from soluble form to insoluble be particles form by serum components. In addition, proteomic analysis of isolated cholesterol particles showed presence of approximately 195 serum prtoteins (Madasamy S, 2014). Therefore, it was of interest to identify serum factors that are involved in the statin mediated modulation of cholesterol particles formation. These factors may directly or indirectly affect the redistribution of LDL, HDL particles, their size, metabolism and functional properties (Zannis VI et al, 2006). Accordingly, to examine the composition of statin induced cholesterol particles, we applied proteomics approach to identify protein markers. Identification of the serum protein markers present in statin-cholesterol complex/particles may help to better understand the metabolism of HDL and LDL particles and their role in pathogenesis of atherosclerosis. To achieve this objective, the statin induced cholesterol particles formed in the serum samples were used for Flow cytometer based sorting followed by isolation of cholesterol particles in a relatively pure form (FIG. 14). Next, the isolated cholesterol particles were subjected to mass spectroscopy based proteomics analysis. Mass spectroscopy analysis of tryptic digests obtained from the cholesterol particles identified approximately 14667 peptide spectra. A database search of the resultant spectra identified approximately 195 serum proteins shown below.

FIG. 14. Flow cytometer assessment and sorter-based isolation of statin induced cholesterol particles. Left, gating of cholesterol particles X axis represents plaque particles detection in green channel (520 nm) and Y axis represents plaque particles detection in yellow channel (560 nm) and Right, sorted cholesterol particles, X axis represents plaque particles detection in forward scattering and Y axis represents plaque particles detection in side scatter.

Identification of serum proteins in the statin induced cholesterol particle: The list of identified serum proteins in statin induced cholesterol particles are: Serum albumin, Cluster of Complement C3, Serotransferrin, Apolipoprotein B-100, Cluster of Ig gamma-1 chain C region, Ig gamma-2 chain C region, Ig gamma-3 chain C region, Cluster of Alpha-2-macroglobulin, Cluster of Complement C4-B, Complement C4-A, Cluster of Keratin, type II cytoskeletal 2 epidermal, Cluster of Alpha-1-antitrypsin, g kappa chain C region, Apolipoprotein A-I, Cluster of Haptoglobin, Isoform 2 of Haptoglobin-related protein, Ceruloplasmin, Isoform 3 of Fibronectin, Cluster of Complement factor H, Cluster of Ig alpha-1 chain C region, Ig alpha-2 chain C region, Plasminogen, Vitamin D-binding protein, Hemopexin, Transthyretin, Cluster of Ig mu chain C region, Inter-alpha-trypsin inhibitor heavy chain H2, Cluster of Inter-alpha-trypsin inhibitor heavy chain H4, Isoform 2 of Inter-alpha-trypsin inhibitor heavy chain H4, Complement factor B, Cluster of Ig lambda-2 chain C regions, Immunoglobulin lambda-like polypeptide 5, Ig lambda-7 chain C region, Ig lambda-6 chain C region, Prothrombin, Alpha-1-antichymotrypsin, Gelsolin, Antithrombin-III, Apolipoprotein A-IV, Alpha-2-HS-glycoprotein, Alpha-1B-glycoprotein, Afamin, Beta-2-glycoprotein 1, Histidine-rich glycoprotein, Inter-alpha-trypsin inhibitor heavy chain H1, Plasma protease C1 inhibitor , Apolipoprotein E, Apolipoprotein A-II, Complement C5, Serum paraoxonase/arylesterase, Angiotensinogen, CD5 antigen-like, Zinc-alpha-2-glycoprotein, Cluster of Desmoplakin, Alpha-1-acid glycoprotein 2, Alpha-1-acid glycoprotein 1, Protein AMBP, Vitronectin, Alpha-2-antiplasmin, Hemoglobin subunit alpha, Isoform 2 of Clusterin, Cluster of Ig kappa chain V-III region, Cluster of Ig kappa chain V-IV region, Pigment epithelium-derived factor, Cluster of Ig kappa chain V-II region TEW, Complement C1s subcomponent, Isoform 2 of Fibrinogen alpha chain, Carboxypeptidase N subunit 2, Ig kappa chain V-II region, Complement component C8 beta chain, Serum amyloid A-4 protein, Complement component C8 alpha chain, Desmoglein-1, Tetranectin, Thyroxine-binding globulin, Apolipoprotein M, Spectrin, Ig mu heavy chain disease protein, Kininogen-1, C4b-binding protein alpha chain, Complement C1r subcomponent, Complement component C7, Heparin cofactor 2, Apolipoprotein D, Complement factor I, Corticosteroid-binding globulin, Complement component C6, Ig heavy chain V-III region TEI, Kallistatin, Ig heavy chain V-III region, Isoform 2 of Ficolin-3, Selenoprotein P, Isoform Short of Heterogeneous nuclear ribonucleoprotein, Retinol-binding protein 4, Cluster of Hemoglobin subunit beta, Complement C2, Isoform Short of Heterogeneous nuclear ribonucleoprotein, Plasma kallikrein, Ig heavy chain V-III region BRO, Isoform 2 of Apolipoprotein L1, Serum amyloid P-component, Filaggrin, Apolipoprotein C-II, Platelet basic protein, Platelet factor 4, Actin, cytoplasmic 1, Lactotransferrin, Isoform 2 of Annexin A2, Isoform 1B of Desmocollin-1, Ig lambda chain V-IV region Hil, Immunoglobulin lambda-like polypeptide 1, Insulin-like growth factor-binding protein complex, Cluster of Ig kappa chain V-I region DEE, Ig kappa chain V-I region AU, Apolipoprotein C-III, Leucine-rich alpha-2-glycoprotein, Complement component C8 gamma chain, Isoform 2 of N-acetylmuramoyl-L-alanine amidase and Complement C1q subcomponent subunit B.

In addition, it will be appreciated that the various results with different statins may be used for testing other lipid modulating drugs that may have synergistic effect for treating, diagnosing and monitoring may use this assay to treat a patient suffering from lipid regulatory disease such as CVD. The examples of anti-atherosclerosis drugs that are used as monotherapy or combination therapy are: (1) statins, niacin and fibrates and (2) small molecules, protein/antibody therapeutics targeting cholesterol esterase transfer protein (CETP) pathway and/or proprotein convertase subtilisin/kexin type 9, also known as PCSK9 pathway. Accordingly, the specification and drawings are to be regarded in an illustrative rather than a restrictive sense.

What is claimed is:

1. A non-enzymatic method, comprising:
    adding a lipid modulating drug at a specific concentration to a solution of a lipid having a second specific concentration to form a lipid-lipid modulating drug solution;
    incubating the lipid-lipid modulating drug solution for a specific time;
    detecting a lipid particle using an identification process as the result of the incubation of the lipid modulating drug with the solution of the lipid.

2. The method of claim 1, wherein the lipid modulating drug is at least one of a ovastatin, simvastatin, atorvastatin, pravastatin, fluvastatin, rosuvastatin and a combination thereof.

3. The method of claim 2, wherein the method produces a result for an efficacy of at least one of the ovastatin, simvastatin, atorvastatin, pravastatin, fluvastatin, rosuvastatin and the combination thereof.

4. The method of claim 2, wherein the combination thereof is at least one of the ovastatin, simvastatin, atorvastatin, pravastatin, fluvastatin, rosuvastatin and another drug.

5. The method of claim 1, wherein the solution of lipid is at least one of a total lipid, derivative of a total lipid, a total cholesterol, a derivative of a cholesterol, total triglycerides, a derivative of a triglyceride and a combination thereof.

6. The method of claim 1, wherein the identification process consists of using a Flow cytometer, Nuclear Magnetic Resonance, ultra-centrifugation, ion mobility, gradient gel electrophoresis, fluorescence particle detectors and colorimetric method.

7. The method of claim 1, wherein the lipid particle has many fractions, wherein the lipid particle fractions are at least one of a total cholesterol, total triglycerides, LDL, HDL, non-HDL lipid and combination thereof.

8. The method of claim 7, wherein one fraction of the lipid particle is lowered and another fraction of the lipid particle is increased.

9. A non-enzymatic method , comprising:
    adding a statin drug at a specific concentration into a biofluid sample to form a lipid statin composition;
    adding a fluorescence lipid aggregate to the lipid-statin composition;
    incubating the statin drug, the fluorescence lipid aggregate and the biofluid sample for a specific time to form a lipid particle, wherein the lipid particle comprises multiple fractions; and
    feeding the lipid particle into a flow cytometer for separation of the fractions and to observe the multiple fractions as separate fractions of the lipid particle.

10. The method of claim 9, wherein the statin drug is at least one of a ovastatin, simvastatin, atorvastatin, pravastatin, fluvastatin, rosuvastatin and a combination thereof.

11. The method of claim 9, wherein the lipid particle is at least one of a total cholesterol, total triglycerides, LDL, HDL, non-HDL lipid and a combination thereof.

12. The method of claim 9, further comprising:
    identifying the separate fractions of the lipid particle; and
    modulating the specific concentration for the statin drug used in the method to get a desirable distribution of the separate fractions of the lipid particle.

13. The method of claim 12, further comprising:
    measuring the separate fractions of the lipid particle for at least one of a total cholesterol particles, total triglycerides particles, LDL particles, HDL particles and non-HDL lipid particles using the biofluid as a response to addition of the statin drug.

14. The method of claim 9, wherein the biofluid is at least one of a serum and plasma.

15. A non-enzymatic method, comprising:
    adding a lipid modulating drug at a specific concentration to a lipid aggregate to form a lipid particle;
    capturing a lipid particle profile formed by the addition of the lipid modulating drug to the lipid aggregate;

modulating the specific concentration of the lipid modulating drug based upon the lipid particle profile; and
adding the modulated specific concentration to a duplicate lipid aggregate to observe an effect of the lipid modulating drug on the lipid particle formed.

16. The method of claim 15, further comprising: modulating a treatment for a patient based on the effect of the lipid modulating drug on the lipid particle.

17. The method of claim 15, further comprising:
making a new lipid modulating drug based on the effect of the lipid modulating drug on the lipid particle.

18. The method of claim 15, wherein the lipid modulating drug is a statin drug, wherein the statin drug is at least one of a ovastatin, simvastatin, atorvastatin, pravastatin, fluvastatin, rosuvastatin and a combination thereof.

19. The method of claim 15, wherein the lipid particle is at least one of total cholesterol particles, total triglycerides, LDL, HDL, non-HDL lipid, and a combination thereof, and the lipid aggregate is provided by a serum sample.

* * * * *